United States Patent [19]

Mullis

[11] Patent Number: 4,683,202

[45] Date of Patent: * Jul. 28, 1987

[54] PROCESS FOR AMPLIFYING NUCLEIC ACID SEQUENCES

[75] Inventor: Kary B. Mullis, Kensington, Calif.

[73] Assignee: Cetus Corporation, Emeryville, Calif.

[ * ] Notice: The portion of the term of this patent subsequent to Jul. 28, 2004 has been disclaimed.

[21] Appl. No.: 791,308

[22] Filed: Oct. 25, 1985

Related U.S. Application Data

[63] Continuation-in-part of Ser. No. 716,975, Mar. 28, 1985, abandoned.

[51] Int. Cl.$^4$ .................... C12P 19/34; C12N 15/00; C12N 1/00; C07H 21/04; C07H 21/02

[52] U.S. Cl. .................... 435/91; 435/177.3; 435/317; 536/27; 536/28; 536/29; 935/17; 935/18; 935/16

[58] Field of Search .................... 435/91, 172.3, 317; 536/27, 28, 29; 935/17, 18

[56] References Cited

PUBLICATIONS

Gaubatz et al, "Strategies for Constructing Complementary DNA for Cloning", J. Theor. Biol. 95: 679 (1982).

Caton and Robertson, *Nucleic Acids Research*, vol. 7, pp. 1445–1456 (1979).

Rossi et al., *J. Biol. Chem.*, 257, 9226–9229 (1982).

*Primary Examiner*—James Martinell
*Attorney, Agent, or Firm*—Janet E. Hasak; Albert P. Halluin

[57] ABSTRACT

The present invention is directed to a process for amplifying any desired specific nucleic acid sequence contained in a nucleic acid or mixture thereof. The process comprises treating separate complementary strands of the nucleic acid with a molar excess of two oligonucleotide primers, and extending the primers to form complementary primer extension products which act as templates for synthesizing the desired nucleic acid sequence. The steps of the reaction may be carried out stepwise or simultaneously and can be repeated as often as desired.

21 Claims, 12 Drawing Figures

FIG. 1

Double-Stranded 94-bp Sequence

```
TTTGC  TTCTGACACA  ACTGTGTTCA  CTAGCAACCT  →
AAACG  AAGACTGTGT  TGACACAAGT  GATCGTTGGA

NcoI        HinfI MstII
               V           V    V
CAAACAGACA  CCATGGTGCA  CCTGACTCCT  GAGGAGAAGT  →
GTTTGTCTGT  GGTACCACGT  GGACTGAGGA  CTCCTCTTCA
                                     ↑
                                    Allelic base
                                    pair DNA
                                    polymorphism

CTGCCGTTAC  TGCCCTGTG
GACGGCAATG  ACGGGACAC
```

FIG. 4-1 Human Betaglobin

```
       101         111         121         131 ***      141         151         161         171         181         191         201         211         221
        |           |           |           |           |           |           |           |           |           |           |           |           |
0  ...CCATCTATTG CTTACATITG CTTCTGACAC AACTGTGTTC ACTAGCAACC ACCTGACTCC TGAGGAGAAG TCTGCCGTTA CTGCCCTGTG GGGCAAGGTG AAGTTGGTGG...
       :::::::::: :::::::::: :::::::::: :::::::::: :::::::::: :::::::::: :::::::::: :::::::::: :::::::::: :::::::::: ::::::::::
0  ...GGTACATAAC GAATGTAAAC GAAGACTGTG TTGACACAAG TGATCGTTGG TGGACTGAGG ACTCCTCTTC AGACGGCAAT GACGGGACAC CCCGTTCCAC TTCAACCACC...

CACAGGGCAGTAACG  PCO1
        +
    TTTGCTTCTGACACA  PCO2

5'  PCO2     TTTG    CTTCTGACAC A ----> extends
                                           :::: :::::::::: :
0  ...GGTACATAAC GAATGTAAAC GAAGACTGTG TTGACACAAG TGATCGTTGG TGGACTGAGG ACTCCTCTTC AGACGGCAAT GACGGGACAC CCCGTTCCAC TTCAACCACC...

|
                                                                                     Polymerase, dNTPs
                                                                                        |
                                                                                        v 0  ...CCATCTATTG CTTACATTTG CTTCTGACAC AACTGTGTTC ACTAGCAACC ACCTGACTCC TGAGGAGAAG TCTGCCGTTA CTGCCCTGTG GGGCAAGGTG AAGTTGGTGG...
       :::::::::: :::::::::: :::::::::: :::::::::: :::::::::: :::::::::: :::::::::: :::::::::: :::::::::: :::::::::: ::::::::::
1  ...GGTACATAAC GAATGTAAAC GAAGACTGTG TTGACACAAG TGATCGTTGG TGGACTGAGG ACTCCTCTTC AGACGGCAAT GACGGGACAC                                                        } 1 CYCLES TTTG CTTCTGACAC AACTGTGTTC ACTAGCAACC ACCTGACTCC TGAGGAGAAG TCTGCCGTTA CTGCCCTGTG GGGCAAGGTG AAGTTGGTGG...
                                :::: :::::::::: :::::::::: :::::::::: :::::::::: :::::::::: :::::::::: :::::::::: :::::::::: :::::::::: ::::::::::
0  ...GGTACATAAC GAATGTAAAC GAAGACTGTG TTGACACAAG TGATCGTTGG TGGACTGAGG ACTCCTCTTC AGACGGCAAT GACGGGACAC CCCGTTCCAC TTCAACCACC...

|
                                                                                      denature,
                                                                                      re-anneal
                                                                                        |
                                                                                        v 0  ...CCATCTATTG CTTACATTTG CTTCTGACAC AACTGTGTTC ACTAGCAACC ACCTGACTCC TGAGGAGAAG TCTGCCGTTA CTGCCCTGTG GGGCAAGGTG AAGTTGGTGG...
                                                                                                  extends <----- GCAAT GACGGGACAC      5' PCO1

5'  PCO2     TTTG    CTTCTGACAC A ----> extends
                                           :::: :::::::::: :
1  ...GGTACATAAC GAATGTAAAC GAAGACTGTG TTGACACAAG TGATCGTTGG TCGACTGAGG ACTCCTCTTC AGACGGCAAT TTTG CTTCTGACAC AACTGTGTTC ACTAGCAACC ACCTGACTCC TGAGGAGAAG TCTGCCGTTA CTGCCCTGTG GGGCAAGGTG AAGTTGGTGG...
1                               :::: :::::::::: :::::::::: :::::::::: :::::::::: :::::::::: :::::::::: :::::::::: :::::::::: :::::::::: ::::::::::      } 2
                                                                                                   extends <----- GCAAT GACGGGACAC      5' PCO1

0  ...GGTAGATAAC GAATGTAAAC GAACACTGTG TTGACACAAG TGATCGTTGG TGGACTGAGG ACTCCTCTTC AGACGGCAAT GACGGGACAC CCCGTTCCAC TTCAACCACC...
```

FIG.4-2

```
                                                                    Polymerase, dNTPs 0 CCATCTATTG CTTACATTTG CTTCTGACAC AACTGTGTTC ACTAGCAACC ACCTGACTCC TGAGGAGAAG TCTGCCGTTA CTGCCCTGTG GGGCAAGGTG AAGTTGGTGG...  ⎤
  ::::::::::  ::::::::::  ::::::::::  ::::::::::  ::::::::::  ::::::::::  ::::::::::  ::::::::::  ::::::::::  ::::::::::  ::::::::::     |
2 GGTAGATAAC GAATGTAAAC GAAGACTGTG TTGACACAAG TGATCGTTGG TGGACTGAGG ACTCCTCTTC AGACGGCAAT GACGGGACAC                          |
                                                                                                                             |
  2     TTTG CTTCTGACAC AACTGTGTTC ACTAGCAACC ACCTGACTCC TGAGGAGAAG TCTGCCGTTA CTGCCCTGTG                                     | 2
        ::::  ::::::::::  ::::::::::  ::::::::::  ::::::::::  ::::::::::  ::::::::::  ::::::::::                              |
1 GGTAGATAAC GAATGTAAAC GAAGACTGTG TTGACACAAG TGATCGTTGG TGGACTGAGG ACTCCTCTTC AGACGGCAAT GACGGGACAC                          |
                                                                                                                             |
  1     TTTG CTTCTGACAC AACTGTGTTC ACTAGCAACC ACCTGACTCC TGAGGAGAAG TCTGCCGTTA CTGCCCTGTG GGGCAAGGTG AAGTTGGTGG...             |
        ::::  ::::::::::  ::::::::::  ::::::::::  ::::::::::  ::::::::::  ::::::::::  ::::::::::  ::::::::::  ::::::::::     |
2     AAAC GAAGACTGTG TTGACACAAG TGATCGTTGG TGGACTGAGG ACTCCTCTTC AGACGGCAAT GACGGGACAC                                       |
                                                                                                                             |
  2     TTTG CTTCTGACAC AACTGTGTTC ACTAGCAACC ACCTGACTCC TGAGGAGAAG TCTGCCGTTA CTGCCCTGTG GGGCAAGGTG AAGTTGGTGG...             |
        ::::  ::::::::::  ::::::::::  ::::::::::  ::::::::::  ::::::::::  ::::::::::  ::::::::::  ::::::::::  ::::::::::     |
0 GGTAGATAAC GAATGTAAAC GAAGACTGTG TTGACACAAG TGATCGTTGG TGGACTGAGG ACTCGTCTTC AGACGGCAAT GACGGGACAC CCCGTTCCAC TTCAACCACC...  ⎦

↓ denature, re-anneal
                                                ↓

0 CCATCTATTG CTTACATTTG CTTCTGACAC AACTGTGTTC ACTAGCAACC ACCTGACTCC TGAGGAGAAG TCTGCCGTTA CTGCCCTGTG GGGCAAGGTG AAGTTGGTGG... ⎤
                                                                            extends <----- GCAAT GACGGGACAC        5' PCO1    |
                                                                                                                              |
5' PCO2 TTTG CTTCTGACAC A -----> extends                                                                                      |
        ::::  :::::::::: :                                                                                                    |
2 GGTAGATAAC GAATGTAAAC GAAGACTGTG TTGACACAAG TGATCGTTGG TGGACTGAGG ACTCCTCTTC AGACGGCAAT GACGGGACAC                            |
                                                                                                                              |
2       TTTG CTTCTGACAC AACTGTGTTC ACTAGCAACC ACCTGACTCC TGAGGAGAAG TCTGCCGTTA CTGCCCTGTG                                      |
                                                                    extends <----- GCAAT GACGGGACAC         5' PCO1           | 3
                                                                                                                              |
5' PCO2 TTTG CTTCTGACAC A -----> extends                                                                                      |
        ::::  :::::::::: :                                                                                                    |
1 GGTAGATAAC GAATGTAAAC GAAGACTGTG TTGACACAAG TGATCGTTGG TGGACTGAGG ACTCCTCTTC AGACGGCAAT GACGGGACAC                            |
                                                                                                                              |
1       TTTG CTTCTGACAC AACTGTGTTC ACTAGCAACC ACCTGACTCC TGAGGAGAAG TCTGCCGTTA CTGCCCTGTG GGGCAAGGTG AAGTTGGTGG...              |
                                                                    extends <----- GCAAT GACGGGACAC         5' PCO1           |
                                                                                                                              |
5' PCO2 TTTG CTTCTGACAC A -----> extends                                                                                      |
        ::::  :::::::::: :                                                                                                    |
2       AAAC GAAGACTGTG TTGACACAAG TGATCGTTGG TGGACTGAGG ACTCCTCTTC AGACGGCAAT GACGGGACAC                                      |
                                                                                                                              |
2       TTTG CTTCTGACAC AACTGTGTTC ACTAGCAACC ACCTGACTCC TGAGGAGAAG TCTGCCGTTA CTGCCCTGTG GGGCAAGGTG AAGTTGGTGG...              |
                                                                    extends <----- GCAAT GACGGGACAC         5' PCO1           |
                                                                                                                              |
5' PCO2 TTTG CTTCTGACAC A -----> extends                                                                                      |
        ::::  :::::::::: :                                                                                                    |
0 GGTAGATAAC GAATGTAAAC GAAGACTGTG TTGACACAAG TGATCGTTGG TGGACTGAGG ACTCCTCTTC AGACGGCAAT GACGGGACAC CCCGTTCCAC TTCAACCACC... ⎦
```

```
     =====-----
CATGGTGCACCTGACTCCTGAGGAGAAGTCTGCCGTTACTGCCCTGTGGGGCAAGGTGAA
GTACCACGTGGACTGAGGACTCCTCTTCAGACGGCAATGACGGGACACCCCGTTCCACTT
     =====-----
```

β^S

```
     =====    *
CATGGTGCACCTGACTCCTGTGGAGAAGTCTGCCGTTACTGCCCTGTGTGGGGCAAGGTGAA
GTACCACGTGGACTGAGGACACCTCTTCAGACGGCAATGACGGGACACCCCGTTCCACTT
     =====
```

\* Marks the mutation (A to T) in the sickle cell gene which disrupts the DdeI site

PROCESS FOR AMPLIFYING NUCLEIC ACID SEQUENCES

This application is a continuation-in-part of copending U.S. application Ser. No. 716,975 filed Mar. 28, 1985, now abandoned.

BACKGROUND OF THE INVENTION

1. Field of the Invention

The present invention relates to a process for amplifying existing nucleic acid sequences. More specifically, it relates to a process for producing any particular nucleic acid sequence from a given sequence of DNA or RNA in amounts which are large compared to the amount initially present. The DNA or RNA may be single- or double-stranded, and may be a relatively pure species or a component of a mixture of nucleic acids. The process of the invention utilizes a repetitive reaction to accomplish the amplification of the desired nucleic acid sequence.

2. Description of Related Disclosures

For diagnostic applications in particular, the target nucleic acid sequence may be only a small portion of the DNA or RNA in question, so that it may be difficult to detect its presence using nonisotopically labeled or end-labeled oligonucleotide probes. Much effort is being expended in increasing the sensitivity of the probe detection systems, but little research has been conducted on amplifying the target sequence so that it is present in quantities sufficient to be readily detectable using currently available methods.

Several methods have been described in the literature for the synthesis of nucleic acids de novo or from an existing sequence. These methods are capable of producing large amounts of a given nucleic acid of completely specified sequence.

One known method for synthesizing nucleic acids de novo involves the organic synthesis of a nucleic acid from nucleoside derivatives. This synthesis may be performed in solution or on a solid support. One type of organic synthesis is the phosphotriester method, which has been utilized to prepare gene fragments or short genes. In the phosphotriester method, oligonucleotides are prepared which can then be joined together to form longer nucleic acids. For a description of this method, see Narang, S. A., et al., *Meth. Enzymol.*, 68, 90 (1979) and U.S. Pat. No. 4,356,270. The patent describes the synthesis and cloning of the somatostatin gene.

A second type of organic synthesis is the phosphodiester method, which has been utilized to prepare a tRNA gene. See Brown, E. L., et al., *Meth. Enzymol.*, 68, 109 (1979) for a description of this method. As in the phosphotriester method, the phosphodiester method involves synthesis of oligonucleotides which are subsequently joined together to form the desired nucleic acid.

Although the above processes for de novo synthesis may be utilized to synthesize long strands of nucleic acid, they are not very practical to use for the synthesis of large amounts of a nucleic acid. Both processes are laborious and time-consuming, require expensive equipment and reagents, and have a low overall efficiency. The low overall efficiency may be caused by the inefficiencies of the synthesis of the oligonucleotides and of the joining reactions. In the synthesis of a long nucleic acid, or even in the synthesis of a large amount of a shorter nucleic acid, many oligonucleotides would need to be synthesized and many joining reactions would be required. Consequently, these methods would not be practical for synthesizing large amounts of any desired nucleic acid.

Methods also exist for producing nucleic acids in large amounts from small amounts of the initial existing nucleic acid. These methods involve the cloning of a nucleic acid in the appropriate host system, where the desired nucleic acid is inserted into an appropriate vector which is used to transform the host. When the host is cultured the vector is replicated, and hence more copies of the desired nucleic acid are produced. For a brief description of subcloning nucleic acid fragments, see Maniatis, T., et al., *Molecular Cloning: A Laboratory Manual*, Cold Spring Harbor Laboratory, pp. 390–401 (1982). See also the techniques described in U.S. Pat. Nos. 4,416,988 and 4,403,036.

A third method for synthesizing nucleic acids, described in U.S. Pat. No. 4,293,652, is a hybrid of the above-described organic synthesis and molecular cloning methods. In this process, the appropriate number of oligonucleotides to make up the desired nucleic acid sequence is organically synthesized and inserted sequentially into a vector which is amplified by growth prior to each succeeding insertion.

The present invention bears some similarity to the molecular cloning method; however, it does not involve the propagation of any organism and thereby avoids the possible hazards or inconvenience which this entails. The present invention also does not require synthesis of nucleic acid sequences unrelated to the desired sequence, and thereby the present invention obviates the need for extensive purification of the product from a complicated biological mixture.

SUMMARY OF THE INVENTION

The present invention resides in a process for amplifying one or more specific nucleic acid sequences present in a nucleic acid or mixture thereof using primers and inducing agents. The extension product of one primer when hybridized to the other becomes a template for the production of the desired specific nucleic acid sequence, and vice versa, and the process is repeated as often as is necessary to produce the desired amount of the sequence. This method is expected to be more efficient than the methods described above for producing large amounts of nucleic acid from a target sequence and to produce such nucleic acid in a comparatively short period of time. The present method is especially useful for amplifying rare species of nucleic acid present in a mixture of nucleic acids for effective detection of such species.

More specifically, the present invention provides a process for amplifying at least one specific nucleic acid sequence contained in a nucleic acid or a mixture of nucleic acids wherein each nucleic acid consists of two separate complementary strands, of equal or unequal length, which process comprises:

(a) treating the strands with two primers, for each different specific sequence being amplified, under conditions such that for each different sequence being amplified an extension product of each primer is synthesized which is complementary to each nucleic acid strand, wherein said primers are selected so as to be substantially complementary to different strands of each specific sequence such that the extension product synthesized from one primer, when it is separated from its complement, can serve as a template for synthesis of the extension product of the other primer;

(b) separating the primer extension products from the templates on which they were synthesized to produce single-stranded molecules; and (c) treating the single-stranded molecules generated from step (b) with the primers of step (a) under conditions such that a primer extension product is synthesized using each of the single strands produced in step (b) as a template.

The steps may be conducted sequentially or simultaneously. In addition, steps (b) and (c) may be repeated until the desired level of sequence amplification is obtained.

In other embodiments the invention relates to methods for diagnosing the presence of specific nucleic acid sequences suspected of being in a sample and diagnostic kits applicable thereto.

The present invention may be useful not only for producing large amounts of an existing nucleic acid of completely specified sequence, but also for producing nucleic acid sequences which are known to exist but are not completely specified. In either case an initial copy of the sequence to be amplified must be available, although it need not be pure or a discrete molecule.

BRIEF DESCRIPTION OF THE DRAWINGS

FIG. 1 illustrates a 94 base pair length sequence of human β-globin desired to be amplified. The single base pair change which is associated with sickle cell anemia is depicted beneath the 94-mer.

FIGS. 4-1-4-3 illustrate in detail the steps and products of the polymerase chain reaction for amplification of the desired 94-mer sequence of human β-globin for three cycles using two oligonucleotide primers.

FIG. 6 illustrates the sequence of the normal ($\beta^A$) and sickle cell ($\beta^S$) β-globin genes in the region of the DdeI and HinfI restriction sites, where the single lines for $\beta^A$ mark the position of the DdeI site (CTGAG) and the double bars for $\beta^A$ and $\beta^S$ mark the position of the HinfI site (GACTC).

DETAILED DESCRIPTION OF THE PREFERRED EMBODIMENTS

Figure 2:
FIG. 2 illustrates an autoradiograph of polyacrylamide gel electrophoresis demonstrating amplification of the 94-mer contained in human wild-type DNA and in a plasmid containing a 1.9 kb BamHI fragment of the normal β-globin gene (pBR328:HbA).

The term "oligonucleotide" as used herein in referring to primers, probes, oligomer fragments to be detected, oligomer controls and unlabeled blocking oligomers is defined as a molecule comprised of two or more deoxyribonucleotides or ribonucleotides, preferably more than three. Its exact size will depend on many factors, which in turn depend on the ultimate function or use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, i.e., in the presence of nucleotides and an inducing agent such as DNA polymerase and at a suitable temperature and pH. The primer is preferably single stranded for maximum efficiency in amplification, but may alternatively be double stranded. If double stranded, the primer is firt treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and use of the method. For example, for diagnostics applications, depending on the complexity of the target sequence, the oligonucleotide primer typically contains 15-25 or more nucleotides, although it may contain fewer nucleotides. For other applications, the oligonucleotide primer is typically shorter, e.g., 7-15 nucleotides. Such short primer molecules generally require cooler temperatures to form sufficiently stable hybrid complexes with template.

The primers herein are selected to be "substantially" complementary to the different strands of each specific sequence to be amplified. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to be amplified to hybridize therewith and thereby form a template for synthesis of the extension product of the other primer.

As used herein, the terms "restriction endonucleases" and "restriction enzymes" refer to bacterial enzymes each of which cut double-stranded DNA at or near a specific nucleotide sequence.

As used herein, the term "DNA polymorphism" refers to the condition in which two or more different nucleotide sequences coexists in the same interbreeding population in a DNA sequence.

The term "restriction fragment length polymorphism" ("RFLP") refers to the differences in DNA nucleotide sequences that are randomly distributed throughout the entire human genome and that produce different restriction endonuclease patterns.

The present invention is directed to a process for amplifying any one or more desired specific nucleic acid sequences found in a nucleic acid. Because large amounts of a specific sequence may be produced by this process, the present invention may be used for improving the efficiency of cloning DNA or messenger RNA and for amplifying a target sequence to facilitate detection thereof. The present invention is also useful for obtaining large amounts of the desired sequence from a mixture of nucleic acids resulting from an imperfect chemical synthesis.

In general, the present process involves a chain reaction for producing, in exponential quantities relative to the number of reaction steps involved, at least one specific nucleic acid sequence given (a) that the ends of the required sequence are known in sufficient detail that oligonucleotides can be synthesized which will hybridize to them, and (b) that a small amount of the sequence is available to initiate the chain reaction. The product of the chain reaction will be a discrete nucleic acid duplex with termini corresponding to the ends of the specific primers employed.

Any source of nucleic acid, in purified or nonpurified form, can be utilized as the starting nucleic acid or acids, provided it contains or is suspected of containing the specific nucleic acid sequence desired. Thus, the process may employ, for example, DNA or RNA, including messenger RNA, which DNA or RNA may be single stranded or double stranded. In addition, a DNA-RNA hybrid which contains one strand of each may be utilized. A mixture of any of these nucleic acids may also be employed, or the nucleic acid produced from a previous amplification reaction herein using the same or different primers may be so utilized. The specific nucleic acid sequence to be amplified may be only a fraction of a larger molecule or can be present initially as a discrete molecule, so that the specific sequence constitutes the entire nucleic acid. It is not necessary that the sequence to be amplified be present initially in a pure form; it may be a minor fraction of a complex mixture, such as a portion of the β-globin gene contained in whole human DNA or a portion of nucleic acid sequence due to a particular microorganism which organism might constitute only a very minor fraction of a particular biological sample. The starting nucleic acid may contain more than one desired specific nucleic acid sequence which may be the same or different. Therefore, the present process is useful not only for producing large amounts of one specific nucleic acid sequence, but also for amplifying simultaneously more than one different specific nucleic acid sequence located on the same or different nucleic acid molecules.

The nucleic acid or acids may be obtained from any source, for example, from plasmids such as pBR322, from cloned DNA or RNA, or from natural DNA or RNA from any source, including bacteria, yeast, viruses, and higher organisms such as plants or animals. DNA or RNA may be extracted from blood, tissue material such as chorionic villi or amniotic cells by a variety of techniques such as that described by Maniatis et al., *Molecular Cloning A Laboratory Manual* (New York: Cold Spring Harbor Laboratory, 1982), pp. 280–281.

Any specific nucleic acid sequence can be produced by the present process. It is only necessary that a sufficient number of bases at both ends of the sequence be known in sufficient detail so that two oligonucleotide primers can be prepared which will hybridize to different strands of the desired sequence and at relative positions along the sequence such that an extension product synthesized from one primer, when it is separated from its template (complement), can serve as a template for extension of the other primer into a nucleic acid of defined length. The greater the knowledge about the bases at both ends of the sequence, the greater can be the specificity of the primers for the target nucleic acid sequence, and thus the greater the efficiency of the process. It will be understood that the word primer as used hereinafter may refer to more than one primer, particularly in the case where there is some ambiguity in the information regarding the terminal sequence(s) of the fragment to be amplified. For instance, in the case where a nucleic acid sequence is inferred from protein sequence information a collection of primers containing sequences representing all possible codon variations based on degeneracy of the genetic code will be used for each strand. One primer from this collection will be 100% homologous with the end of the desired sequence to be amplified.

The oligonucleotide primers may be prepared using any suitable method, such as, for example, the phosphotriester and phosphodiester methods described above, or automated embodiments thereof. In one such automated embodiment diethylphosphoramidites are used as starting materials and may be synthesized as described by Beaucage et al., *Tetrahedron Letters* (1981), 22: 1859–1962. One method for synthesizing oligonucleotides on a modified solid support is described in U.S. Pat. No. 4,458,066. It is also possible to use a primer which has been isolated from a biological source (such as a restriction endonuclease digest).

The specific nucleic acid sequence is produced by using the nucleic acid containing that sequence as a template. If the nucleic acid contains two strands, it is necessary to separate the strands of the nucleic acid before it can be used as the template, either as a separate step or simultaneously with the synthesis of the primer extension products. This strand separation can be accomplished by any suitable method including physical, chemical or enzymatic means. One physical method of separating the strands of the nucleic acid involves heating the nucleic acid until it is completely (>99%) denatured. Typical heat denaturation may involve temperatures ranging from about 80° to 105° C. for times ranging from about 1 to 10 minutes. Strand separation may also be induced by an enzyme from the class of enzymes known as helicases or the enzyme RecA, which has helicase activity and in the presence of riboATP is known to denature DNA. The reaction conditions suitable for separating the strands of nucleic acids with helicases are described by Cold Spring Harbor Symposia on Quantitative Biology, Vol. XLIII "DNA: Replication and Recombination" (New York: Cold Spring Harbor Laboratory, 1978), B. Kuhn et al., "DNA Helicases", pp. 63–67, and techniques for using RecA are reviewed in C. Radding, *Ann. Rev. Genetics.* 16: 405–37 (1982).

If the original nucleic acid containing the sequence to be amplified is single stranded, its complement is synthesized by adding one or two oligonucleotide primers thereto. If an appropriate single primer is added, a primer extension product is synthesized in the presence of the primer, an inducer or catalyst of the synthesis and the four nucleotides described below. The product will be partially complementary to the single-stranded nucleic acid and will hybridize with the nucleic acid strand to form a duplex of unequal length strands that may then be separated into single strands as described above to produce two single separated complementary strands. Alternatively, two appropriate primers may be added to the single-stranded nucleic acid and the reaction carried out.

If the original nucleic acid constitutes the sequence to be amplified, the primer extension product(s) produced will be completely complementary to the strands of the original nucleic acid and will hybridize therewith to form a duplex of equal length strands to be separated into single-stranded molecules.

When the complementary strands of the nucleic acid or acids are separated, whether the nucleic acid was originally double or single stranded, the strands are ready to be used as a template for the synthesis of additional nucleic acid strands. This synthesis can be performed using any suitable method. Generally it occurs in a buffered aqueous solution, preferably at a pH of 7–9, most preferably about 8. Preferably, a molar excess (for cloned nucleic acid, usually about 1000:1 primer:template, and for genomic nucleic acid, usually about $10^6$:1 primer:template) of the two oligonucleotide primers is added to the buffer containing the separated template strands. It is understood, however, that the amount of complementary strand may not be known if the process herein is used for diagnostic applications, so that the amount of primer relative to the amount of complementary strand cannot be determined with certainty. As a practical matter, however, the amount of primer added will generally be in molar excess over the amount of complementary strand (template) when the sequence to be amplified is contained in a mixture of complicated long-chain nucleic acid strands. A large molar excess is preferred to improve the efficiency of the process.

The deoxyribonucleoside triphosphates dATP, dCTP, dGTP and TTP are also added to the synthesis mixture in adequate amounts and the resulting solution is heated to about 90°–100° C. for from about 1 to 10 minutes, preferably from 1 to 4 minutes. After this heating period the solution is allowed to cool to room temperature, which is preferable for the primer hybridization. To the cooled mixture is added an appropriate agent for inducing or catalyzing the primer extension reaction, and the reaction is allowed to occur under conditions known in the art. This synthesis reaction may occur at from room temperature up to a temperature above which the inducing agent no longer functions efficiently. Thus, for example, if DNA polymerase is used as inducing agent, the temperature is generally no greater than about 40° C. Most conveniently the reaction occurs at room temperature.

The inducing agent may be any compound or system which will function to accomplish the synthesis of primer extension products, including enzymes. Suitable enzymes for this purpose include, for example, *E. coli* DNA polymerase I, Klenow fragment of *E. coli* DNA polymerase I, T4 DNA polymerase, other available DNA polymerases, reverse transcriptase, and other enzymes, including heat-stable enzymes, which will facilitate combination of the nucleotides in the proper manner to form the primer extension products which are complementary to each nucleic acid strand. Generally, the synthesis will be initiated at the 3' end of each primer and proceed in the 5' direction along the template strand, until synthesis terminates, producing molecules of different lengths. There may be inducing agents, however, which initiate synthesis at the 5' end and proceed in the other direction, using the same process as described above.

The newly synthesized strand and its complementary nucleic acid strand form a double-stranded molecule which is used in the succeeding steps of the process. In the next step, the strands of the double-stranded molecule are separated using any of the procedures described above to provide single-stranded molecules.

New nucleic acid is synthesized on the single-stranded molecules. Additional inducing agent, nucleotides and primers may be added if necessary for the reaction to proceed under the conditions prescribed above. Again, the synthesis will be initiated at one end of the oligonucleotide primers and will proceed along the single strands of the template to produce additional nucleic acid. After this step, half of the extension product will consist of the specific nucleic acid sequence bounded by the two primers.

The steps of strand separation and extension product synthesis can be repeated as often as needed to produce the desired quantity of the specific nucleic acid sequence. As will be described in further detail below, the amount of the specific nucleic acid sequence produced will accumulate in an exponential fashion.

When it is desired to produce more than one specific nucleic acid sequence from the first nucleic acid or mixture of nucleic acids, the appropriate number of different oligonucleotide primers are utilized. For example, if two different specific nucleic acid sequences are to be produced, four primers are utilized. Two of the primers are specific for one of the specific nucleic acid sequences and the other two primers are specific for the second specific nucleic acid sequence. In this manner, each of the two different specific sequences can be produced exponentially by the present process.

The present invention can be performed in a step-wise fashion where after each step new reagents are added, or simultaneously, where all reagents are added at the initial step, or partially step-wise and partially simultaneous, where fresh reagent is added after a given number of steps. If a method of strand separation, such as heat, is employed which will inactivate the inducing agent, as in the case of a heat-labile enzyme, then it is necessary to replenish the inducing agent after every strand separation step. The simultaneous method may be utilized when an enzymatic means is used for the strand separation step. In the simultaneous procedure, the reaction mixture may contain, in addition to the nucleic acid strand(s) containing the desired sequence, the strand-separating enzyme (e.g., helicase), an appropriate energy source for the strand-separating enzyme, such as rATP, the four nucleotides, the oligonucleotide primers in molar excess, and the inducing agent, e.g., Klenow fragment of *E. coli* DNA polymerase I. If heat is used for denaturation in a simultaneous process, a heat-stable inducing agent such as a thermostable polymerase may be employed which will operate at an elevated temperature, preferably 65°–90° C. depending on the inducing agent, at which temperature the nucleic acid will consist of single and double strands in equilibrium. For smaller lengths of nucleic acid, lower temperatures of about 50° C. may be employed. The upper temperature will depend on the temperature at which the enzyme will degrade or the temperature above which an insufficient level of primer hybridization will occur. Such a heat-stable enzyme is described, e.g., by A. S. Kaledin et al., *Biokhimiya*, 45, 644–651 (1980). Each step of the process will occur sequentially notwithstanding the initial presence of all the reagents. Additional materials may be added as necessary. After the appropriate length of time has passed to produce the desired amount of the specific nucleic acid sequence, the reaction may be halted by inactivating the enzymes in any known manner or separating the components of the reaction.

The process of the present invention may be conducted continuously. In one embodiment of an automated process, the reaction may be cycled through a denaturing region, a reagent addition region, and a reaction region. In another embodiment, the enzyme used for the synthesis of primer extension products can be immobilized in a column. The other reaction components can be continuously circulated by a pump through the column and a heating coil in series; thus the nucleic acids produced can be repeatedly denatured without inactivating the enzyme.

desired sequence [S] comprised of complementary strands [S+] and [S−] is utilized as the nucleic acid. During the first and each subsequent reaction cycle extension of each oligonucleotide primer on the original template will produce one new ssDNA molecule product of indefinite length which terminates with only one of the primers. These products, hereafter referred to as "long products," will accumulate in a linear fashion; that is, the amount present after any number of cycles will be proportional to the number of cycles.

The long products thus produced will act as templates for one or the other of the oligonucleotide primers during subsequent cycles and will produce molecules of the desired sequence [S+] or [S−]. These molecules will also function as templates for one or the other of the oligonucleotide primers, producing further [S+] and [S−], and thus a chain reaction can be sustained which will result in the accumulation of [S] at an exponential rate relative to the number of cycles.

By-products formed by oligonucleotide hybridizations other than those intended are not self-catalytic (except in rare instances) and thus accumulate at a linear rate.

The specific sequence to be amplified, [S], can be depicted diagrammatically as:

```
[S+]  5' AAAAAAAAAAXXXXXXXXXXCCCCCCCCCC 3'
[S−]  3' TTTTTTTTTTYYYYYYYYYYGGGGGGGGGG 5'
```

The appropriate oligonucleotide primers would be:

Primer 1: GGGGGGGGGG
Primer 2: AAAAAAAAAA so that if DNA containing [S]

```
. . . zzzzzzzzzzzzzzzzAAAAAAAAAAXXXXXXXXXXCCCCCCCCCCzzzzzzzzzzzzzzzz . . .
. . . zzzzzzzzzzzzzzzzTTTTTTTTTTYYYYYYYYYYGGGGGGGGGGzzzzzzzzzzzzzzzz . . .
``` is separated into single strands and its single strands are hybridized to Primers 1 and 2, the following extension reactions can be catalyzed by DNA polymerase in the presence of the four deoxyribonucleoside triphosphates:

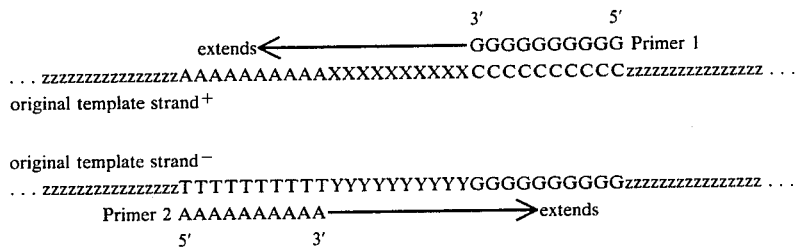

The present invention is demonstrated diagrammatically below were double-stranded DNA containing the On denaturation of the two duplexes formed, the products are:

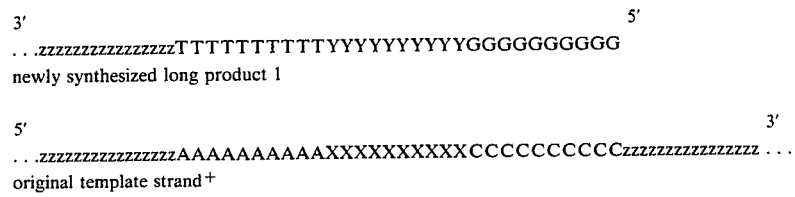

-continued

```
3'                                                                          5'
. . .zzzzzzzzzzzzzzzzzTTTTTTTTTTYYYYYYYYYGGGGGGGGGGzzzzzzzzzzzzzzzz . . .
original template strand 5'                                                         3'
               AAAAAAAAAAXXXXXXXXXXCCCCCCCCCCzzzzzzzzzzzzzzzz . . .
               newly synthesized long product 3
```

If these four strands are allowed to rehybridize with Primers 1 and 2 in the next cycle, inducing agent will catalyze the following reactions:

```
     Primer 2   5' AAAAAAAAAA ──────────────────────→extends to here
3' . . . zzzzzzzzzzzzzzzzzzTTTTTTTTTTYYYYYYYYYGGGGGGGGGG 5'
newly synthesized long product 1 extends←──────────────────── GGGGGGGGGG 5' Primer 1
5' . . .zzzzzzzzzzzzAAAAAAAAAAXXXXXXXXXXCCCCCCCCCCzzzzzzzzzzzz . . . 3'
original template strand +

Primer 2   5' AAAAAAAAAA─────────────────────→extends
3' . . . zzzzzzzzzzzzzzzzzzTTTTTTTTTTYYYYYYYYYGGGGGGGGGGzzzzzzzzz . . . 5'
original template strand − extends to here ←─────────────────GGGGGGGGGG 5' Primer 1
         5' AAAAAAAAAAXXXXXXXXXXCCCCCCCCCCzzzzzzzzzzzzzz . . . 3'
         newly synthesized long product 2
```

If the strands of the above four duplexes are separated, the following strands are found:

```
5' AAAAAAAAAAXXXXXXXXXXCCCCCCCCCC 3'
newly synthesized [S+]
3' . . . zzzzzzzzzzzzzzzzzzTTTTTTTTTTYYYYYYYYYYGGGGGGGGGG 5'
first cycle synthesized long product 1
3' . . . zzzzzzzzzzzzzzzzzzTTTTTTTTTTYYYYYYYYYYGGGGGGGGGG 5'
newly synthesized long product 1
5' . . . zzzzzzzzzzzzzzzzzzzzzAAAAAAAAAAXXXXXXXXXXCCCCCCCCCCzzzzzzzzz . . . 3'
original template strand +
5' AAAAAAAAAAXXXXXXXXXXCCCCCCCCCCzzzzzzzzzzzzzzzz . . . 3'
newly synthesized long product 2
3' . . . zzzzzzzzzzzzzTTTTTTTTTTYYYYYYYYYYGGGGGGGGGGzzzzzzzzzzzzzzzz . . . 5'
original template strand −
3' TTTTTTTTTTYYYYYYYYYYGGGGGGGGGG 5'
newly synthesized [S−]
5' AAAAAAAAAAXXXXXXXXXXCCCCCCCCCCzzzzzzzzzzzzzzzz . . . 3'
first cycle synthesized long product 2
```

It is seen that each strand which terminates with the oligonucleotide sequence of one primer and the complementary sequence of the other is the specific nucleic acid sequence [S] that is desired to be produced.

The steps of this process can be repeated indefinitely, being limited only by the amount of Primers 1 and 2, inducing agent and nucleotides present. The amount of original nucleic acid remains constant in the entire process, because it is not replicated. The amount of the long products increases linearly because they are produced only from the original nucleic acid. The amount of the specific sequence increases exponentially. Thus, the specific sequence will become the predominant species. This is illustrated in the following table, which indicates the relative amounts of the species theoretically present after n cycles, assuming 100% efficiency at each cycle:

Number of Double Strands
After 0 to n Cycles

| Cycle Number | Template | Long Products | Specific Sequence [S] |
|---|---|---|---|
| 0 | 1 | — | — |
| 1 | 1 | 1 | 0 |
| 2 | 1 | 2 | 1 |
| 3 | 1 | 3 | 4 |
| 5 | 1 | 5 | 26 |
| 10 | 1 | 10 | 1013 |
| 15 | 1 | 15 | 32,752 |
| 20 | 1 | 20 | 1,048,555 |
| n | 1 | n | $(2^n - n - 1)$ |

When a single-stranded nucleic acid is utilized as the template, only one long product is formed per cycle.

The method herein may be utilized to clone a particular nucleic acid sequence for insertion into a suitable expression vector. The vector may then be used to transform an appropriate host organism to produce the gene product of the sequence by standard methods of recombinant DNA technology.

In addition, the process herein can be used for in vitro mutagenesis. The oligodeoxyribonucleotide primers need not be exactly complementary to the DNA sequence which is being amplified. It is only necessary that they be able to hybridize to the sequence sufficiently well to be extended by the polymerase enzyme or by whatever other inducing agent is employed. The product of a polymerase chain reaction wherein the primers employed are not exactly complementary to the original template will contain the sequence of the primer rather than the template, thereby introducing an in vitro mutation. In further cycles this mutation will be amplified with an undiminished efficiency because no further mispaired primings are required. The mutant thus produced may be inserted into an appropriate vector by standard molecular biological techniques and might confer mutant properties on this vector such as the potential for production of an altered protein.

The process of making an altered DNA sequence as described above could be repeated on the altered DNA using different primers so as to induce further sequence changes. In this way a series of mutated sequences could gradually be produced wherein each new addition to the series could differ from the last in a minor way, but from the original DNA source sequence in an increasingly major way. In this manner changes could be made ultimately which were not feasible in a single step due to the inability of a very seriously mismatched primer to function.

In addition, the primer can contain as part of its sequence a non-complementary sequence provided that a sufficient amount of the primer contains a sequence which is complementary to the strand to be amplified. For example, a nucleotide sequence which is not complementary to the template sequence (such as, e.g., a promoter, linker, coding sequence, etc.) may be attached at the 5' end of one or both of the primers, and thereby appended to the product of the amplification process. After the extension primer is added, sufficient cycles are run to achieve the desired amount of new template containing the non-complementary nucleotide insert. This allows production of large quantities of the combined fragments in a relatively short period of time (e.g., two hours or less) using a simple technique.

The method herein may also be used to enable detection and/or characterization of specific nucleic acid sequences associated with infectious diseases, genetic disorders or cellular disorders such as cancer. Amplification is useful when the amount of nucleic acid available for analysis is very small, as, for example, in the prenatal diagnosis of sickle cell anemia using DNA obtained from fetal cells. Amplification is particularly useful if such an analysis is to be done on a small sample using non-radioactive detection techniques which may be inherently insensitive, or where radioactive techniques are being employed but where rapid detection is desirable.

For purposes of this invention genetic diseases may include specific deletions and/or mutations in genomic DNA from any organism, such as, e.g., sickle cell anemia, cystic fibrosis, α-thalassemia, β-thalassemia, and the like. Sickle cell anemia can be readily detected via oligomer restriction analysis or a RFLP-like analysis following amplification of the appropriate DNA sequence by the present method. α-Thalassemia can be detected by the absence of a sequence, and β-thalassemia can be detected by the presence of a polymorphic restriction site closely linked to a mutation which causes the disease.

All of these genetic diseases may be detected by amplifying the appropriate sequence and analyzing it by Southern blots without using radioactive probes. In such a process, for example, a small sample of DNA from, e.g., amniotic fluid containing a very low level of the desired sequence is amplified, cut with a restriction enzyme, and analyzed via a Southern blotting technique. The use of non-radioactive probes is facilitated by the high level of the amplified signal.

In another embodiment a small sample of DNA may be amplified to a convenient level and then a further cycle of extension reactions performed wherein nucleotide derivatives which are readily detectable (such as $^{32}$P-labeled or biotin labeled nucleoside triphosphates) are incorporated directly into the final DNA product, which may be analyzed by restriction and electrophoretic separation or any other appropriate method. An example of this technique in a model system is demonstrated in FIG. 5.

Figure 3:
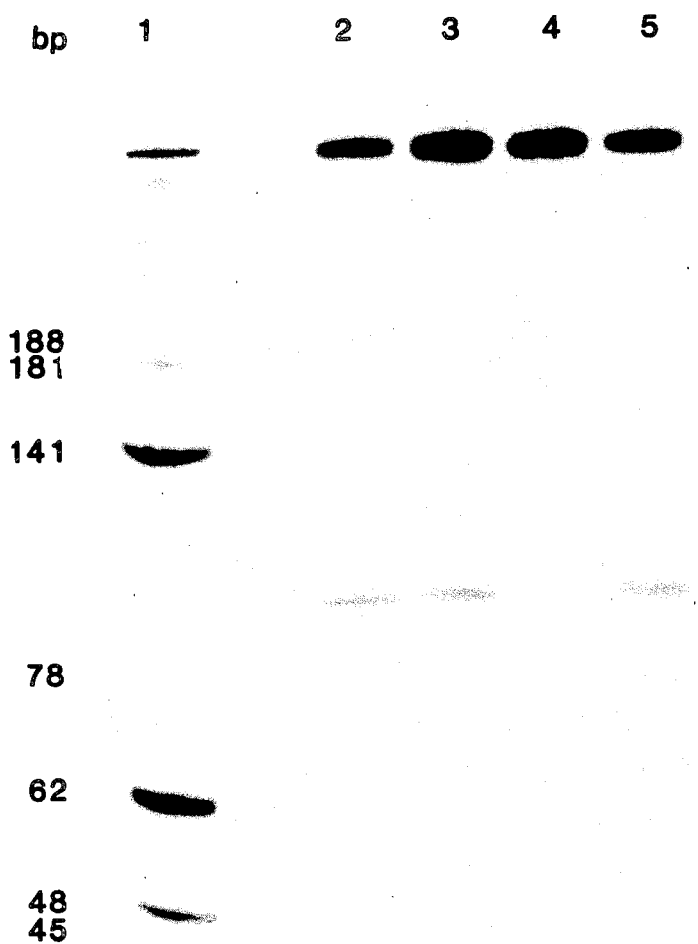
FIG. 3 illustrates an autoradiograph of polyacrylamide gel electrophoresis demonstrating amplification of any of the specific target 94-mer sequence present in pBR328:HbA, a plasmid containing a 1.9 kb BamHI fragment of the sickle cell allele of β-globin (pBR328:HbS), pBR328:HbA where the sequence to be amplified is cleaved with MstII, and pBR328:HbS where the sequence to the amplified has been treated but not cleaved with MstII.

In a further embodiment, demonstrated in a model system in FIG. 3, the nucleic acid may be exposed to a particular restriction endonuclease prior to amplification. Since a sequence which has been cut cannot be amplified, the appearance of an amplified fragment, despite prior restriction of the DNA sample, implies the absence of a site for the endonuclease within the amplified sequence. The presence or absence of an amplified sequence can be detected by an appropriate method.

Figure 7:
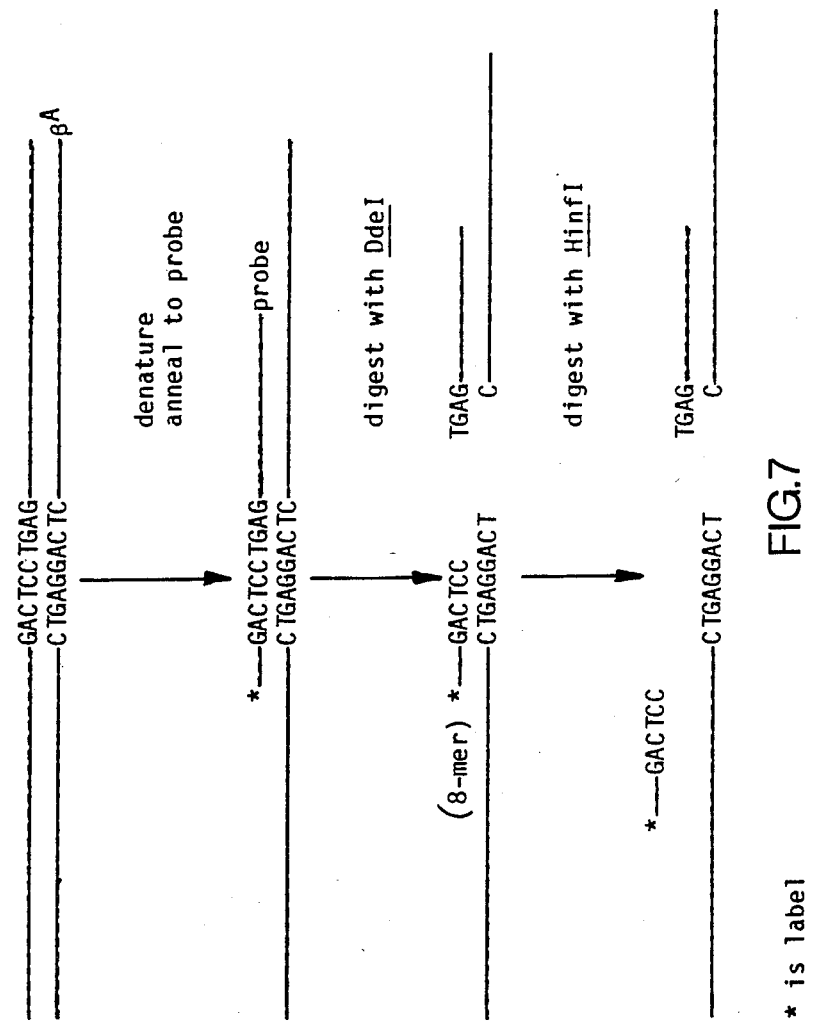
FIG. 7 illustrates the results of sequential digestion of normal β-globin using a 40-mer probe and DdeI followed by HinfI restriction enzymes.
Figure 8:
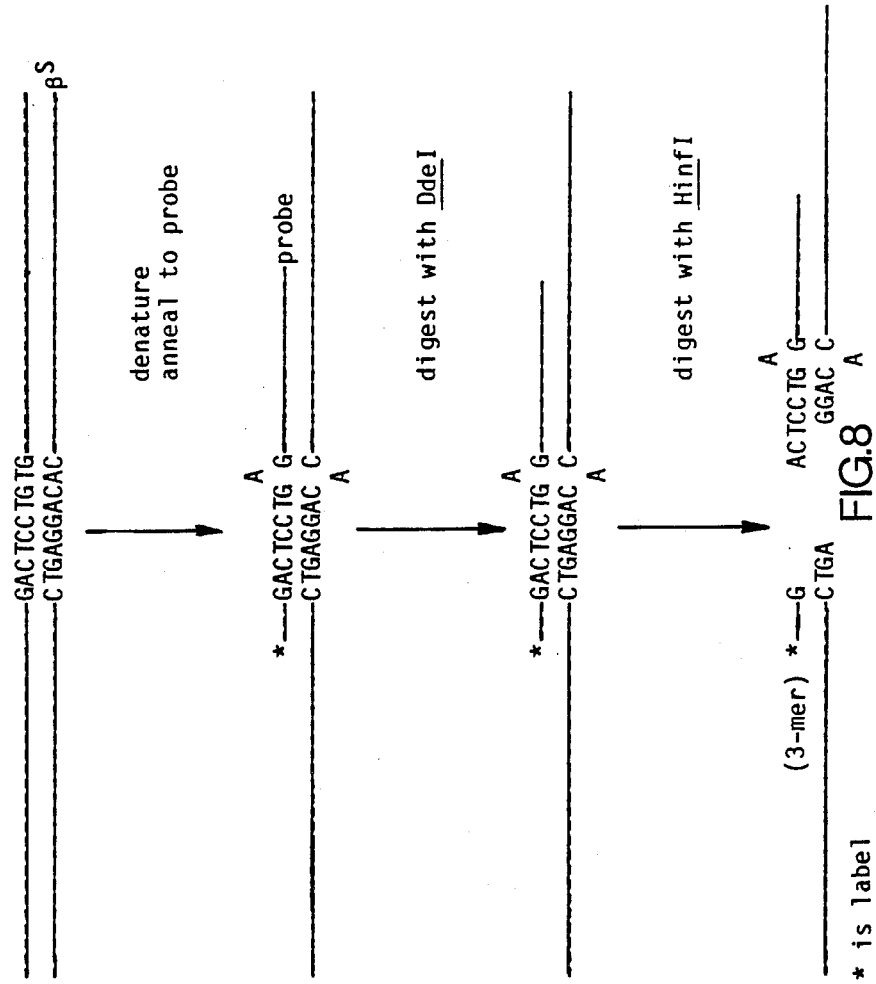
FIG. 8 illustrates the results of sequential digestion of sickle β-globin using the same 40-mer probe as in FIG. 7 and DdeI followed by HinfI restriction enzymes.

A practical application of this technique can be illustrated by its use in facilitating the detection of sickle cell anemia via the oligomer restriction technique described herein and in copending U.S. application Ser. No. 716,982 to Erlich et al. entitled "Method For Detection of Polymorphic Restriction Sites and Nucleic Acid Sequences" filed Mar. 28, 1985. Sickle cell anemia is a hemoglobin disease which is caused by a single base pair change in the sixth codon of the β-globin gene. FIG. 6 illustrates the sequences of normal and sickle cell β-globin genes in the region of their polymorphism, where the single bars mark the location of a DdeI site present only in the normal gene and where the double bars mark the location of a HinfI site which is non-polymorphic and thus present in both the normal and sickle cell alleles. FIG. 7 illustrates the process of oligomer restriction of normal β-globin DNA using a probe spanning both restriction sites and labeled where the asterisk appears. The DNA, amplified as provided herein, is denatured and annealed to the labeled probe. The enzyme DdeI cleaves the DNA at the reformed DdeI site and generates a labeled octamer. Under the conditions used in the test the octamer is short enough to dissociate from the duplex. The subsequent addition of the enzyme HinfI has no effect on the now single-stranded octamer. FIG. 8 illustrates the same process applied to the sickle cell allele of β-globin DNA. The enzyme DdeI cannot cleave the duplex formed by the amplified DNA and the labeled probe because of the A—A base pair mismatch. The enzyme HinfI, however, does restrict the hybrid and a labeled trimer is produced. In practice the method can diagnose the DNA of an individual as being either homozygous for the wild type, homozygous for the sickle type or a heterozygous carrier of the sickle cell trait, since a specific signal is associated with the presence of either allele. Use of this above-described method to amplify the pertinent sequence allows for a rapid analysis of a single copy gene using a probe with only a single $^{32}$P label.

Various infectious diseases can be diagnosed by the presence in clinical samples of specific DNA sequences characteristic of the causative microorganism. These include bacteria, such as Salmonella, Chlamydia, and Neisseria; viruses, such as the hepatitis viruses; and protozoan parasites, such as the Plasmodium responsible for malaria. U.S. Pat. No. 4,358,535 issued to Falkow describes the use of specific DNA hybridization probes for the diagnosis of infectious diseases. A problem inherent in the Falkow procedure is that a relatively small number of pathogenic organisms may be present in a clinical sample from an infected patient and the DNA extracted from these may constitute only a very small fraction of the total DNA in the sample. Specific amplification of suspected sequences prior to immobilization and hybridization detection of the DNA samples could greatly improve the sensitivity and specificity of these procedures.

Routine clinical use of DNA probes for the diagnosis of infectious diseases would be simplified considerably if non-radioactively labeled probes could be employed as described in EP 63,879 to Ward. In this procedure biotin-containing DNA probes are detected by chromogenic enzymes linked to avidin or biotin-specific antibodies. This type of detection is convenient, but relatively insensitive. The combination of specific DNA amplification by the present method and the use of stably labeled probes could provide the convenience and sensitivity required to make the Falkow and Ward procedures useful in a routine clinical setting.

The amplification process can also be utilized to produce sufficient quantities of DNA from a single copy human gene such that detection by a simple non-specific DNA stain such as ethidium bromide can be employed so as to make a DNA diagnosis directly.

In addition to detecting infectious diseases and pathological abnormalities in the genome of organisms, the process herein can also be used to detect DNA polymorphism which may not be associated with any pathological state.

The following examples are offered by way of illustration and are not intended in limit the invention in any manner. In these examples all percentages are by weight if for solids and by volume if for liquids, and all temperatures are in degrees Celsius unless otherwise noted.

EXAMPLE 1

A 25 base pair sequence having the nucleotide sequence

5' CCTCGGCACCGTCACCCTGGATGCT 3'

3' GGAGCCGTGGCAGTGGGACCTACGA 5' contained on a 47 base pair FokI restriction fragment of pBR322 obtainable from ATCC was prepared as follows. A FokI digest of pBR322 containing the 47-bp fragment was produced by digesting pBR322 with FokI in accordance with the conditions suggested by the supplier, New England Biolabs Inc. The primers which were utilized were 5' d(CCTCGGCACCG) 3' and 5' d(AGCATCCAGGGTG) 3', and were prepared using conventional techniques. The following ingredients were added to 33 µl of buffer which consisted of 25 mM potassium phosphate, 10 mM magnesium chloride and 100 mM sodium chloride at pH 7.5: 2433 pmoles of each of the primers described above, 2.4 pmoles of the FokI digest of pBR322, 12 nmoles of dATP, 22 nmoles of dCTP, 19 nmoles of dGTP and 10 nmoles of TTP.

The mixture was heated to 85° C. for five minutes and allowed to cool to ambient temperature. Five units of the Klenow fragment of E. coli DNA polymerase I were added and the temperature was maintained for 15 minutes. After that time, the mixture was again heated to 85° C. for five minutes and allowed to cool. Five units of the Klenow fragment were again added and the reaction was carried out for 15 minutes. The heating, cooling and synthesis steps were repeated eleven more times.

After the final repetition, a 5µl aliquot was removed from the reaction mixture. This was heated to 85° C. for three minutes and allowed to cool to ambient temperature. 12.5 pmoles of α-P$^{32}$-deoxycytidine triphosphate and 5 units of Klenow fragment were added and the reaction was allowed to proceed for 15 minutes. The labeled products were examined by polyacrylamide gel electrophoresis. The FokI digest was labeled in a similar fashion and served as a control and molecular weight markers. The only heavily labeled band visible after the 13 cycles was the intended 25 base pair sequence.

EXAMPLE 2

The desired sequence to be amplified was a 94 base pair sequence contained within the human beta-globin gene and spanning the MstII site involved in sickle cell anemia. The sequence has the nucleotide sequence shown in FIG. 1.

I. Synthesis of Primers

The following two oligodeoxyribonucleotide primers were prepared by the method described below:

5' CACAGGGCAGTAACG 3' Primer A and

5' TTTGCTTCTGACACA 3' Primer B

Automated Synthesis Procedures: The diethylphosphoramidites, synthesized according to Beaucage and Caruthers (*Tetrahedron Letters* (1981) 22:1859–1862), were sequentially condensed to a nucleoside derivatized controlled pore glass support using a Biosearch SAM-1. The procedure included detritylation with trichloroacetic acid in dichloromethane, condensation using benzotriazole as activating proton donor, and capping with acetic anhydride and dimethylaminopyridine in tetrahydrofuran and pyridine. Cycle time was approximately 30 minutes. Yields at each step were essentially quantitative and were determined by collection and spectroscopic examination of the dimethoxytrityl alcohol released during detritylation.

Oligodeoxyribonucleotide Deprotection and Purification Procedures: The solid support was removed from the column and exposed to 1 ml concentrated ammonium hydroxide at room temperature for four hours in a closed tube. The support was then removed by filtration and the solution containing the partially protected oligodeoxyribonucleotide was brought to 55° C. for five hours. Ammonia was removed and the residue was applied to a preparative polyacrylamide gel. Electrophoresis was carried out at 30 volts/cm for 90 minutes after which the band containing the product was identified by UV shadowing of a fluorescent plate. The band was excised and eluted with 1 ml distilled water overnight at 4° C. This solution was applied to an Altech RP18 column and eluted with a 7–13% gradient of acetonitrile in 1% ammonium acetate buffer at pH 6.0. The elution was monitored by UV absorbance at 260 nm and the appropriate fraction collected, quantitated by UV absorbance in a fixed volume and evaporated to dryness at room temperature in a vacuum centrifuge.

Characterization of Oligodeoxyribonucleotides: Test aliquots of the purified oligonucleotides were $^{32}$P labeled with polynucleotide kinase and $\gamma$-$^{32}$P-ATP. The labeled compounds were examined by autoradiography of 14-20% polyacrylamide gels after electrophoresis for 45 minutes at 50 volts/cm. The procedure verifies the molecular weight. Base composition was determined by digestion of the oligodeoxyribonucleotide to nucleosides by use of venom diesterase and bacterial alkaline phosphatase and subsequent separation and quantitation of the derived nucleosides using a reverse phase HPLC column and a 10% acetonitrile, 1% ammonium acetate mobile phase.

II. Source of DNA

A. Extraction of Whole Human Wild-Type DNA

Human genomic DNA homozygous for normal $\beta$-globin was extracted from the cell line Molt4 (obtained from Human Genetic Mutant Cell Repository and identified as GM2219c) using the technique described by Stetler et al., Proc. Nat. Acad. Sci. USA (1982), 79:5966-5970.

B. Construction of Cloned Globin Genes

A 1.9 kb BamHI fragment of the normal $\beta$-globin gene was isolated from the cosmid pFC11 and inserted into the BamHI site of pBR328 (Soberon, et al., Gene (1980) 9:287-305). This fragment, which encompasses the region that hybridizes to the synthetic 40-mer probe, includes the first and second exons, first intron, and 5' flanking sequences of the gene (Lawn et al., Cell (1978), 15:1157-1174). This clone was designated pBR328:HbA and deposited under ATCC No. 39,698 on May 25, 1984.

The corresponding 1.9 kb BamHI fragment of the sickle cell allele of $\beta$-globin was isolated from the cosmid pFC12 and cloned as described above. This clone was designated pBR328:HbS and deposited under ATCC No. 39,699 on May 25, 1984.

Each recombinant plasmid was transformed into and propagated in E. coli MM294 (ATCC No. 39,607).

C. Digestion of Cloned Globin Genes with MstII

A total of 100 $\mu$g each of pBR328:HbA and pBR328:HbS were individually digested with 20 units of MstII (New England Biolabs) for 16 hours at 37° C. in 200 $\mu$l of 150 mM NaCl, 12 mM Tris HCl (pH 7.5), 12 mM MgCl$_2$, 1 mM dithiothreitol (DTT), and 100 $\mu$g/ml bovine serum albumin (BSA). The products are designated pBR328:HbA/MstII and pBR328:HbS/MstII, respectively.

III. Polymerase Chain Reaction

To 100 $\mu$l of buffer consisting of 60 mM sodium acetate, 30 mM Tris acetate and 10 mM magnesium acetate at pH 8.0 was added 2 $\mu$l of a solution containing 100 picomoles of Primer A (of the sequence d(CACAGG-GCACTAACG)), 100 picomoles of Primer B (of the sequence d(TTTBCTTCTGACACA)) and 1000 picomoles each of dATP, dCTP, dGTP and TTP. In addition, one of the following sources of DNA described above was added:

10 $\mu$g whole human wild-type DNA (Reaction I)
0.1 picomole pBR328:HbA (Reaction II)
0.1 picomole pBR328:HbS (Reaction III)
0.1 picomole pBR328:HbA/MstII (Reaction IV)
0.1 picomole pBR328:HbS/MstII (Reaction V)
No target DNA (Reaction VI)

Each resulting solution was heated to 100° C. for four minutes and allowed to cool to room temperature for two minutes, whereupon 1 $\mu$l containing four units of Klenow fragment of E. coli DNA polymerase was added. Each reaction was allowed to proceed for 10 minutes, after which the cycle of adding the primers, nucleotides and DNA, heating, cooling, adding polymerase, and reacting was repeated nineteen times for Reaction I and four times for Reactions II-VI.

Four microliter aliquots of Reactions I and II removed before the first cycle and after the last cycle of each reaction were applied to a 12% polyacrylamide gel 0.089M in Tris-borate buffer at pH 8.3 and 2.5 mM in EDTA. The gel was electrophoresed at 25 volts/cm for four hours, transferred to a nylon membrane serving as solid phase support and probed with a 5'-$^{32}$P-labeled 40 bp synthetic fragment, prepared by standard techniques, of the sequence

in 30% formamide, 3×SSPE, 5×Denhardt's, 5% sodium dodecyl sulfate at pH 7.4. FIG. 2 is an autoradiograph of the probed nylon membrane for Reactions I and II. Lane 1 is 0.1 picomole of a 58-bp synthetic fragment control one strand of which is complementary to the above probe. Lane 2 is 4 $\mu$l of Reaction I prior to the first amplification cycle. Lane 3 is 4 $\mu$l of Reaction I after the 20th amplification cycle. Lane 4 is 4 $\mu$l of Reaction II after five amplification cycles. Lane 5 is a molecular weight standard consisting of a FokI (New England Biolabs) digest of pBR322 (New England Biolabs) labeled with alpha-$^{32}$P-dNTPs and polymerase. Lane 3 shows that after twenty cycles the reaction mixture I contained a large amount of the specific sequence of the proper molecular weight and no other detectable products. Reaction mixture II after five cycles also contained this product, as well as the starting nucleic acid and other products, as shown by Lane 4.

To 5.0 $\mu$l aliquots of Reactions II-VI after the fourth cycle were added 5 pmoles of each primer described above. The solutions were heated to 100° C. for four minutes and allowed to equilibrate to room temperature. Three pmoles each of alpha-$^{32}$P-dATP, alpha-$^{32}$P-dCTP, alpha-$^{32}$P-dGTP and alpha-$^{32}$P-TTP and four units of Klenow fragment were added. The reaction, in a final volume of 10 $\mu$l and at the salt concentrations given above, was allowed to proceed for 10 minutes. The polymerase activity was terminated by heating for 20 minutes at 60° C. Four $\mu$l aliquots of Reactions II-VI were loaded onto a 12% polyacrylamide gel 0.089M in Tris-borate buffer at pH 8.3 and 2.5 mM in EDTA. The gel was electrophoresed at 25 volts/cm for four hours after which autoradiography was performed.

FIG. 3 is an autoradiograph of the electrophoresis. Lane 1 is a molecular weight standard, Lane 2 is Reaction II, Lane 3 is Reaction III, Lane 4 is Reaction IV and Lane 5 is Reaction V. Another lane for Reaction VI with no DNA as control had no images in any of the lanes. It can be seen from the figure that the 94--bp fragment predicted from the target DNA was present only where intact $\beta$-globin DNA sequences were available for amplification, i.e., pBR328: HbA (Lane 2), pBR328: HbS (Lane 3) and pBR328: HbS/MstII (Lane 5). MstII digestion cuts pBR328: HbA in the 94-mer sequence rendering it incapable of being amplified, and the 94-mer band does not appear in Lane 4. In contrast, the 94-mer sequence in pBR328: HbS does not cut when the plasmid is digested with MstII and thus is available for amplification as shown in Lane 5.

Figures 3, 4:
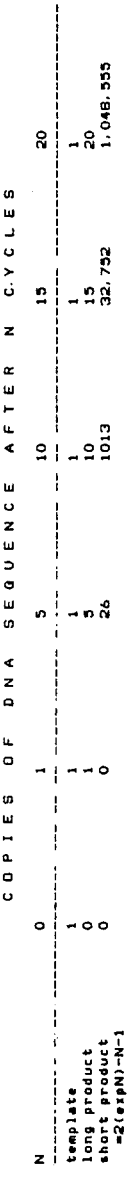

FIG. 4 illustrates the chain reaction for three cycles in amplifying the 94-bp sequence. PC01 and PC02 are Primers A and B. The numbers on the right indicate the cycles, whereas the numbers on the left indiciates the cycle number in which a particular molecule was produced.

EXAMPLE 3

This example illustrates amplification of a 110 bp sequence spanning the allelic MstII site in the human hemoglobin gene.

A total of 1.0 microgram whole human DNA, 100 picomoles D(ACACAACTGTGTTCACTAGC) and 100 picomoles (dCAACTTCATCCACGTTCACC), the primers having been prepared by the technique of Example 2, were dissolved in 100 μl of a solution which was:

1.5 mM in each of the four deoxyribonucleoside triphosphates
30 mM in Tris acetate buffer at pH 7.9
60 mM in sodium acetate
10 mM in magnesium acetate
0.25 mM in dithiothreitol The solution was heated to 100° C. for one minute and brought rapidly to 25° C. for one minute, after which was added 2.5 units Klenow fragment of DNA polymerase. The polymerase reaction was allowed to proceed for two minutes at 25° C., after which the cycle of heating, cooling, adding Klenow, and reacting was repeated as often as desired.

With a 70% efficiency at each cycle, 15 cycles resulted in the synthesis of 1.4 femtomoles of the desired 110 bp fragment of the β-globin gene.

EXAMPLE 4

This example illustrates amplification of a 240 bp sequence spanning the allelic MstII site in the human hemoglobin gene. This sequence contains NcoI, HinfI and MstII restriction sites.

Figure 5:
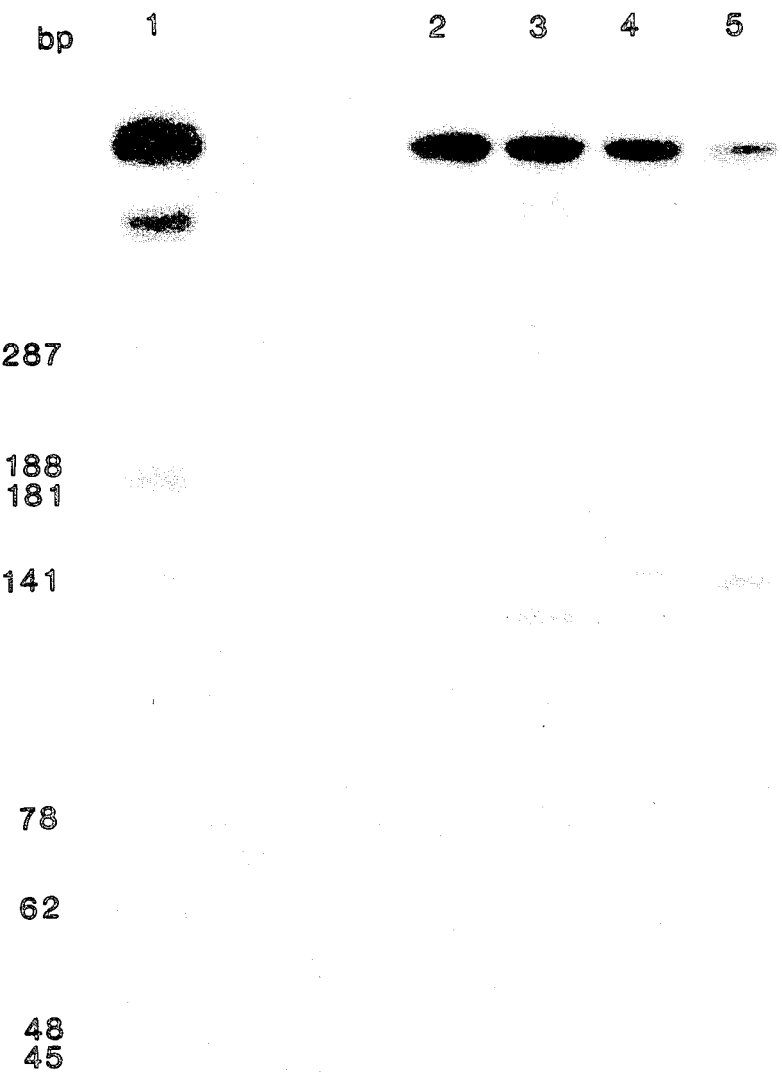
FIG. 5 represents an autoradiograph of polyacrylamide gel electrophoresis demonstrating amplification after four cycles of a 240-mer sequence in pBR328:HbA, where the aliquots are digested with NcoI (Lane 3), MstII (Lane 4) or HinfI (Lane 5). Lane 1 is the molecular weight standard and Lane 2 contains the intact 240-bp product.

To 100 μl of a mixture of 60 mM sodium acetate, 30 mM Tris acetate and 10 mM magnesium acetate at pH 8.0 containing 0.1 pmole pBR328: HbA was added 2 μof Solution A containing:

100 pmoles d(GGTTGGCCAATCTACTCCAGG) primer
100 pmoles d(TAACCTTGATAC-CAACCTGCCC) primer
1000 pmoles each of dATP, dCTP, dGTP and TTP The two primers were prepared by the technique described in Example 2. The solution was heated to 100° C. for four minutes and allowed to cool in ambient air for two minutes, after which was added 1 μl containing four units Klenow fragment of *E. coli* DNA polymerase. The reaction was allowed to proceed for 10 minutes after which the cycle of solution A addition, heating, cooling, adding polymerase, and reacting was repeated three times. To a 5.0 μl aliquot of the reactions was added 5 picomoles of each oligonucleotide primer described above. The solution was heated to 100° C. for four minutes and allowed to come to ambient temperature, after which 3 picomoles each of the alpha-$^{32}$P-labeled deoxyribonucleoside triphosphates and 4 units Klenow fragment were added. The reaction, in a final volume of 10 μl and at the salt concentrations given above, was allowed to proceed for 10 minutes. The polymerase activity was terminated by heating for 20 minutes at 60° C. Two μl aliquots were digested with NcoI, MstII, or HinfI and loaded onto a 12% polyacrylamide gel 0.089M in Tris-borate buffer at pH 8.3 and 2.5 mM in EDTA. The gel was electrophoresed at 25 volts/cm for four hours and autoradiography was performed. FIG. 5 illustrates the autoradiograph of the electrophoresis, were Lane 1 is the molecular weight standard, Lane 2 is without digestion with enzyme (240 bp intact), Lane 3 is digestion with NcoI (131 and 109 bp), Lane 4 is digestion with MstII (149 and 91 bp), and Lane 5 is digestion with HinfI (144 and 96 bp). The autoradiograph is consistent with the amplification of the 240 bp sequence.

EXAMPLE 5

This example illustrates use of the process herein to detect sickle cell anemia by sequential digestion.

Synthesis and Phosphorylation of Oligodeoxyribonucleotides

A labeled DNA probe, RS06, of the sequence
5' *CTGACTCCTGAGGAGAAGTCTGCCGT-TACTGCCCTGTGGG 3'
where * indicates the label, and an unlabeled blocking oligomer, RS10, of the sequence:
3' GACAGAGGTCACCTCTTCAGACG-GCAATGACGGGACACCC 5'
which has three pair mismatches with RS06 were synthesized according to the procedures provided in Example 2(I). The probe RS06 was labeled by contacting five pmole thereof with 4 units of T4 polynucleotide kinase (New England Biolabs) and 50 pmole γ-$^{32}$P-ATP (New England Nuclear, about 7200 Ci/mmole) in a 40 μl reaction volume containing 70 mM Tris buffer (pH 7.6), 10 mM MgCl$_2$, 1.5 mM spermine, and 2.5 mM dithiothreitol for 90 minutes at 37° C. The total volume was then adjusted to 100 μl with 25 mM EDTA and purified according to the procedure of Maniatis et al., Molecular Cloning: A Laboratory Manual (New York: Cold Spring Harbor Laboratory, 1982), pp. 464–465 over a 1 ml Bio Gel P-4 spin dialysis column from Bio-Rad equilibrated with Tris-EDTA (TE) buffer (10 mM Tris buffer, 0.1 mM EDTA, pH 8.0). The labeled probe was further purified by electrophoresis on a 18% polyacrylamide gel (19:1 acrylamide:BIS, Bio-Rad) in Tris-boric acid-EDTA (TBE) buffer (89 mM Tris, 89 mM boric acid, 2.5 mM EDTA, pH 8.3) for 500 vhr. After localization by autoradiography, the portion of the gel containing the labeled probe was excised, crushed and eluted into 0.2 ml TE buffer overnight at 4° C. TCA precipitation of the reaction product indicated that the specific activity was 4.9 Ci/mmole and the final concentration was 20 pmole/ml.

The unlabeled RS10 blocking oligomer was used at a concentration of 200 pmole/ml.

Isolation of Human Genomic DNA from Cell Lines

High molecular weight genomic DNA was isolated from the lymphoid cell lines Molt4, SC-1 and GM2064 using essentially the method of Stetler et al., Proc. Natl. Acad. SC1. USA (1982), 79, 5966–5970 (for Molt4) and Maniatis et al., Molecular Cloning: A Laboratory Manual (New York: Cold Spring Harbor Laboratory, 1982), pp. 280–281

Molt4 (Human Mutant Cell Repository, GM2219C) is a T cell line homozygous for normal β-globin, and SC-1, deposited with ATCC on Mar. 19, 1985, is an EBV-transformed B cell line homozygous for the sickle cell allele. GM2064 (Human Mutant Cell Repository, GM2064) was originally isolated from an individual homozygous for hereditary persistance of fetal hemoglobin (HPFH) and contains no beta- or delta- globin gene sequences. All cell lines were maintained in RPMI-1640 with 10% fetal calf serum.

Isolation of Human Genomic DNA from Clinical Blood Samples

A clinical blood sample designated CH12 from a known sickle cell carrier (AS) was obtained from Dr. Bertram Lubin of Children's Hospital in Oakland, Calif. Genomic DNA was prepared from the buffy coat fraction, which is composed primarily of peripheral blood lymphocytes, using a modification of the procedure described by Nunberg et al., Proc. Nat. Acad. Sci. U.S.A., 75, 5553-5556 (1978).

The cells were resuspended in 5 ml Tris-EDTA-NaCl (TEN) buffer (10 mM Tris buffer pH 8, 1 mM EDTA, 10 mM NaCl) and adjusted to 0.2 mg/ml proteinase K, 0.5% SDS, and incubated overnight at 37° C. Sodium perchlorate was then added to 0.7 M and the lysate gently shaken for 1-2 hours at room temperature. The lysate was extracted with 30 ml phenol/chloroform (1:1), then with 30 ml chloroform, and followed by ethanol precipitation of the nucleic acids. The pellet was resuspended in 2 ml of TE buffer and RNase A added to 0.005 mg/ml. After digestion for one hour at 37° C., the DNA was extracted once each with equal volumes of phenol, phenol/chloroform, and chloroform, and ethanol precipitated. The DNA was resuspended in 0.5 ml TE buffer and the concentration was determined by absorbance at 260 nm.

Polymerase Chain Reaction to Amplify Selectively β-Globin Sequences

Two micrograms of genomic DNA was amplified in an initial 100 μl reaction volume containing 10 mM Tris buffer (ph 7.5), 50 mM NaCl, 10 mM $MgCl_2$, 150 pmole of Primer A of the sequence d(CACAGGGCACTAACG), and 150 pmole of Primer B of the sequence d(CTTTGCTTCTGACACA) and overlayed with about 100 μl mineral oil to prevent evaporation.

Each DNA sample underwent 15 cycles of amplification where one cycle is composed of three steps:
(1) Denature in a heat block set at 95° C. for two minutes.
(2) Transfer immediately to a heat block set at 30° C. for two minutes to allow primers and genomic DNA to anneal.
(3) Add 2 μl of a solution containing 5 units of the Klenow fragment of E. coli DNA polymerase I (New England Biolabs), 1 nmole each of dATP, dCTP, dGTP and TTP, in a buffer composed of 10 mM Tris (pH 7.5), 50 mM NaCl, 10 mM $MgCl_2$, and 4 mM dithiothreitol. This extension reaction was allowed to proceed for 10 minutes at 30° C.

After the final cycle, the reaction was terminated by heating at 95° C. for two minutes. The mineral oil was extracted with 0.2 ml of chloroform and discarded. The final reaction volume was 130 μl.

Hybridization/Digestion of Amplified Genomic DNA with Probes and DdeI/HinfI

Forty-five microliters of the amplified genomic DNA was ethanol precipitated and resuspended in an equal volume of TE buffer. Ten microliters (containing the pre-amplification equivalent of 154 ng of genomic DNA) was dispensed into a 1.5 ml Microfuge tube and 20 μl of TE buffer to a final volume of 30 μl. The sample was overlayed with mineral oil and denatured at 95° C. for 10 minutes. Ten microliters of 0.6 M NaCl containing 0.02 pmole of labeled RS06 probe was added to the tube, mixed gently, and immediately transferred to a 56° C. heat block for one hour. Four microliters of unlabeled RS10 blocking oligomer (0.8 pmole) was added and the hybridization continued for an additional 10 minutes at the same temperature. Five microliters of 60 mM $MgCl_2$/0.1% BSA and 1 μl of DdeI (10 units, New England Biolabs) were added and the reannealed DNA was digested for 30 minutes at 56° C. One microliter of HinfI (10 units, New England Biolabs) was then added and incubated for another 30 minutes. The reaction was stopped by the addition of 4 μl 75 mM EDTA and 6 μl tracking dye to a final volume of 61 μl.

The mineral oil was extracted with 0.2 ml chloroform, and 18 μl of the reaction mixture (45 ng genomic DNA) was loaded onto a 30% polyacrylamide mini-gel (19:1, Bio-Rad) in a Hoeffer SE200 apparatus. The gel was electrophoresed at approximately 300 volts for one hour until the bromphenol blue dye front migrated to 3.0 cm offorigin. The top of 1.5 cm of the gel was removed and the remaining gel was exposed for four days with one intensification screen at −70° C.

Figure 9:
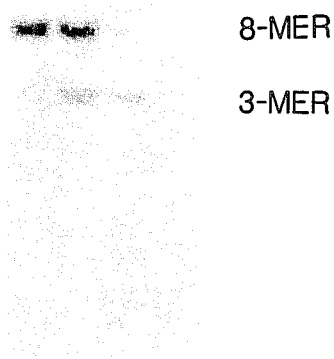
FIG. 9 illustrates an autoradiograph of polyacrylamide gel electrophoresis demonstrating the use of the same 40-mer probe as in FIG. 7 to specifically characterize the beta-globin alleles present in samples of whole human DNA which have been subjected to amplification by the present method.

Discussion of Autoradiograph (FIG. 9)

Each lane contains 45 ng of amplified genomic DNA. Lane A contains Molt4 DNA; Lane B, CH12; Lane C, SC-1; and Lane D, GM2064. Molt4 represents the genotype of a normal individual with two copies of the $\beta^A$ gene per cell (AA), CH12 is a clinical sample from a sickle cell carrier with one $\beta^A$ and one $\beta^S$ gene per cell (AS), and SC-1 represents the genotype of a sickle cell individual with two copies of the $\beta^S$ gene per cell (SS). GM2064, which contains no beta- or delta-globin sequences, is present as a negative control.

As seen in the autoradiogram, the DdeI-cleaved, $\beta^A$-specific octamer is present only in those DNA's containing the $\beta^A$ gene (Lanes A and B), and the HinfI-cleaved, $\beta^S$-specific trimer is present only in those DNA's containing the $\beta^S$ gene (Lanes B and C). The presence of both trimer and octamer (Lane B) is diagnostic for a sickle cell carrier and is distinguishable from a normal individual (Lane A) with only octamer and a sickle cell afflicted individual (Lane C) with only trimer.

As a comparison, repeating the experiment described above using non-amplified genomic DNA revealed that the amplification increased the sensitivity of detection by at least 1000 fold.

EXAMPLE 6

This example illustrates direct detection of a totally unpurified single copy gene in whole human DNA on gels without the need for a labeled probe.

Using the technique described in Example 3, a 110-bp fragment from a sequence in the first exon of the beta-globin gene was amplified from 10 micrograms of whole human DNA after 20 cycles. This 110-bp fragment produced after 20 cylces was easily visualized on gels stained with ethidium bromide.

The sequence was not amplified when it was first cut with the restriction enzyme DdeI unless, as in the beta-globin S allele, the sequence does not contain the restriction site recognized by the enzyme.

EXAMPLE 7

A. A total of 100 fmoles pBR328 containing a 1.9 kb insert from the human beta-globin A allele, 50 nmoles each alpha-32P-dNTP at 500 Ci/mole, and 1 nmole of each of the primers used in Example 3 were dissolved in a solution containing 100 μl 30 mM Tris-acetate at pH 7.9, 60 mM sodium acetate, 100 mM dithiothreitol, and 10 mM magnesium acetate. This solution was brought to 100° C. for two minutes and cooled to 25° C. for one minute. A total of 1 μl containing 4.5 units Klenow fragment of E. coli DNA polymerase I and 0.09 units inorganic pyrophosphatase was added to prevent the possible build-up of pyrophosphate in the reaction mixture, and the reaction was allowed to proceed for two minutes at 25° C., after which the cycle of heating, cooling, adding enzyme, and reacting was repeated nine times. Ten-μl aliquots were removed and added to 1 μl 600 mM EDTA after each synthesis cycle. Each was analyzed on a 14% polyacrylamide gel in 90 mM Tris-borate and 2.5 mM EDTA at pH 8.3 and 24 volts/cm for 2.5 hours. The completed gel was soaked for 20 minutes in the same buffer with the addition of 0.5 μg/ml ethidium bromide, washed with the original buffer, and photographed in UV light using a red filter.

The 110-bp fragment produced was excised from the gel under ultraviolet light and the incorporated $^{32}p$ counted by Cerenkov radiation. An attempt to fit the data to an equation of the form: pmoles/10 μl=0.01 $[(1+y)^N - yN - 1]$, where N represents the number of cycles and y the fractional yield per cycle, was optimal with y=0.619. This indicates that a significant amplification is occurring.

B. The above experiment was repeated except that 100 nmoles of each dNTP was added to a 100 μl reaction, no radiolabel was employed, and aliquots were not removed at each cycle. After 10 cycles the reaction was terminated by boiling for two minutes and rehybridization was performed at 57° C. for one hour. The sequence of the 110-bp product was confirmed by subjecting 8 μl aliquots to restriction analysis by addition of 1 μl bovine serum albumin (25 mg/ml) and 1 μl of the appropriate restriction enzyme (HinfI, MnlI, MstII, NcoI) and by reaction at 37° C. for 15 hours. PAGE was performed as described above.

EXAMPLE 8

This example illustrates the use of different primers to amplify various fragments of pBR328 and 322.

A. The experiment described in Example 7A was repeated except using the following primers: d(TTTGCTTCTGACACAACTGTGTTCAC-TAGC) and d(GCCTCACCACCAACTTCATC-CACGTTCACC) to produce a 130-bp fragment of pBR328.

B. The experiment described in Example 7A was repeated except using the following primers: d(GGTTGGCCAATCTACTCCCAGG) and d(TGGTCTCCTTAAACCTGTCTTG) to produce a 262-bp fragment of pBR328. The reaction time was 20 minutes per cycle.

C. The experiment described in Example 8B was repeated except that 100 fmoles of an MstII digest of pBR328 containing a 1.9 kb insert from the human beta-globin S allele was used as initial template. This plasmid was cleaved several times by MstII but not inside the sequence to be amplified. In addition, the primers employed were as follows:
d(GGTTGGCCAATCTACTCCCAGG) and
d(TAACCTTGATACCAACCTGCCC)
to produce a 240-bp fragment.

D. The experiment described in Example 7B was repeated except that 100 fmoles of an NruI digest of pBR322 was used as template, 200 nmoles of each dNTP were used in the 100 μl reaction, and the primers were:
d(TAGGCGTATCACGAGGCCCT) and
d(CTTCCCCATCGGTGATGTCG) to produce a 500-bp fragment from pBR322. Reaction times were 20 minutes per cycle at 37° C. Final rehybridization was 15 hours at 57° C. Electrophoresis was on a 4% agarose gel.

EXAMPLE 9

This example illustrates the invention process wherein an in vitro mutation is introduced into the amplified segment.

A. A total of 100 fmoles of pBR322 linearized with NruI, 1 nmole each of the primers:
d(CGCATTAAAGCTTATCGATG) and
d(TAGGCGTATCACGAGGCCCT)
designed to produce a 75-bp fragment, 100 nmole each dNTP, in 100 μl 40 mM Tris at pH 8, 20 mM in MgCl₂, 5 mM in dithiothreitol, and 5 mg/ml bovine serum albumin were combined. The mixture was brought to 100° C. for one minute, cooled for 0.5 minutes in a water bath at 23° C., whereupon 4.5 units Klenow fragment and 0.09 units inorganic pyrophosphatase were added, and a reaction was allowed to proceed for three minutes. The cycle of heating, cooling, adding enzymes, and reacting was repeated nine times. The tenth reaction cycle was terminated by freezing and an 8-μl aliquot of the reaction mixture was applied to a 4% agarose gel visualized with ethidium bromide.

B. The experiment described in Example 9A was repeated except that the oligonucleotide primers employed were:
d(CGCATTAAAGCTTATCGATG) and
d(AATTAATACGACTCACTATAAGG-GAGATAGGCGTATCACGAGGCCCT).

These primers are designed to produce a 101-bp fragment, 26 nucleotides of which (in the second listed primer) are not present in pBR322. These nucleotides represent the sequence of the T7 promoter, which was appended to the 75-bp sequence from pBR322 by using the primer with 20 complementary bases and a 26-base 5' extension. The procedure required less than two hours and produced two picomoles of the relatively pure 101-bp fragment from 100 fmoles of pBR322.

The T7 promoter can be used to initiate RNA transcription. T7 polymerase may be added to the 101-bp fragment to produce singlestranded RNA.

C. The experiment described in Example 8D was repeated except that the oligonucleotide primers employed were as follows:
d(TAGGCGTATCACGAGGCCCT) and
d(CCAGCAAGACGTAGCCCAGC)
to produce a 1000-bp fragment from pBR322.

D. The experiment described in Example 9C was repeated except that the oligonucleotide primers employed were as follows:
d(TAGGCGTATCACGAGGCCCT) and
d(AATTAATACGACTCACTATAGG-GAGATAGGCGTATCACGAGGCCCT)
so as to produce a 1026-bp fragment, 26 nucleotides of which (in the second listed primer) are not present in pBR322 and represent the T7 promoter described above. The promoter has been inserted adjacent to a 1000-bp fragment from pBR322.

The results indicate that a primer which is not a perfect match to the template sequence but which is nonetheless able to hybridize sufficiently to be enzymatically extended produces a long product which contains the sequence of the primer rather than the corresponding sequence of the original template. The long product serves as a template for the second primer to introduce an in vitro mutation. In further cycles this mutation is amplified with an undiminished efficiency, because no further mispaired primings are required. In this case, a primer which carries a non-complementary extension on its 5' end was used to insert a new sequence in the product adjacent to the template sequence being copied.

E. Because the reaction with polymerase generates pyrophosphate and is theoretically reversible (Kornberg, A., DNA Replication, W. H. Freeman, San Francisco, 1980), the effect of including an inorganic pyrophosphatase to avoid potential pyrophosphorolysis of the product was examined. Qualitative polyacrylamide gel electrophoresis examination of reactions plus and minus pyrophosphatase demonstrated a minor but significant increase in homogeneity of product as a result of the inclusion of this enzyme.

EXAMPLE 10

This example illustrates employing nested sets of primers to decrease the background in the amplification of single copy genes.

Whole human DNA homozygous for the wild-type betaglobin allele was subjected to twenty cycles of amplification as follows: A total of 10 μg DNA, 200 picomoles each of the primers:

d(ACACAACTGTGTTCACTAGC) and
d(CAACTTCATCCACGTTCACC)

and 100 nanomoles each dNTP in 100 μl of 30 mM Tris-acetate pH 7.9, 60 mM sodium acetate, 10 mM dithiothreitol, and 10 mM magnesium acetate were heated to 100° C. for one minute, cooled to 25° C. for one minute, and treated with 2 units Klenow fragment for two minutes. The cycle of heating, cooling and adding Klenow was repeated 19 times. A ten-μl aliquot was removed from the reaction mixture and subjected to a further ten cycles of amplification using each of the primers:

d(CAGACACCATGGTGCACCTGACTCCTG) and
d(CCCCACAGGGCAGTAACG-GCAGACTTCTCC), which amplify a 58-bp fragment contained within the 110-bp fragment produced above. This final ten cycles of amplification was accomplished by diluting the 10-μl aliquot into 90 μl of the fresh Tris-acetate buffer described above containing 100 nanomoles each dNTP and 200 pmoles of each primer. Reaction conditions were as above. After ten cycles a 10-μl aliquot (corresponding to 100 nanograms of the original DNA) was applied to a 6% NuSieve (FMC Corp.) agarose gel and visuallized using ethidium bromide.

Figure 10:
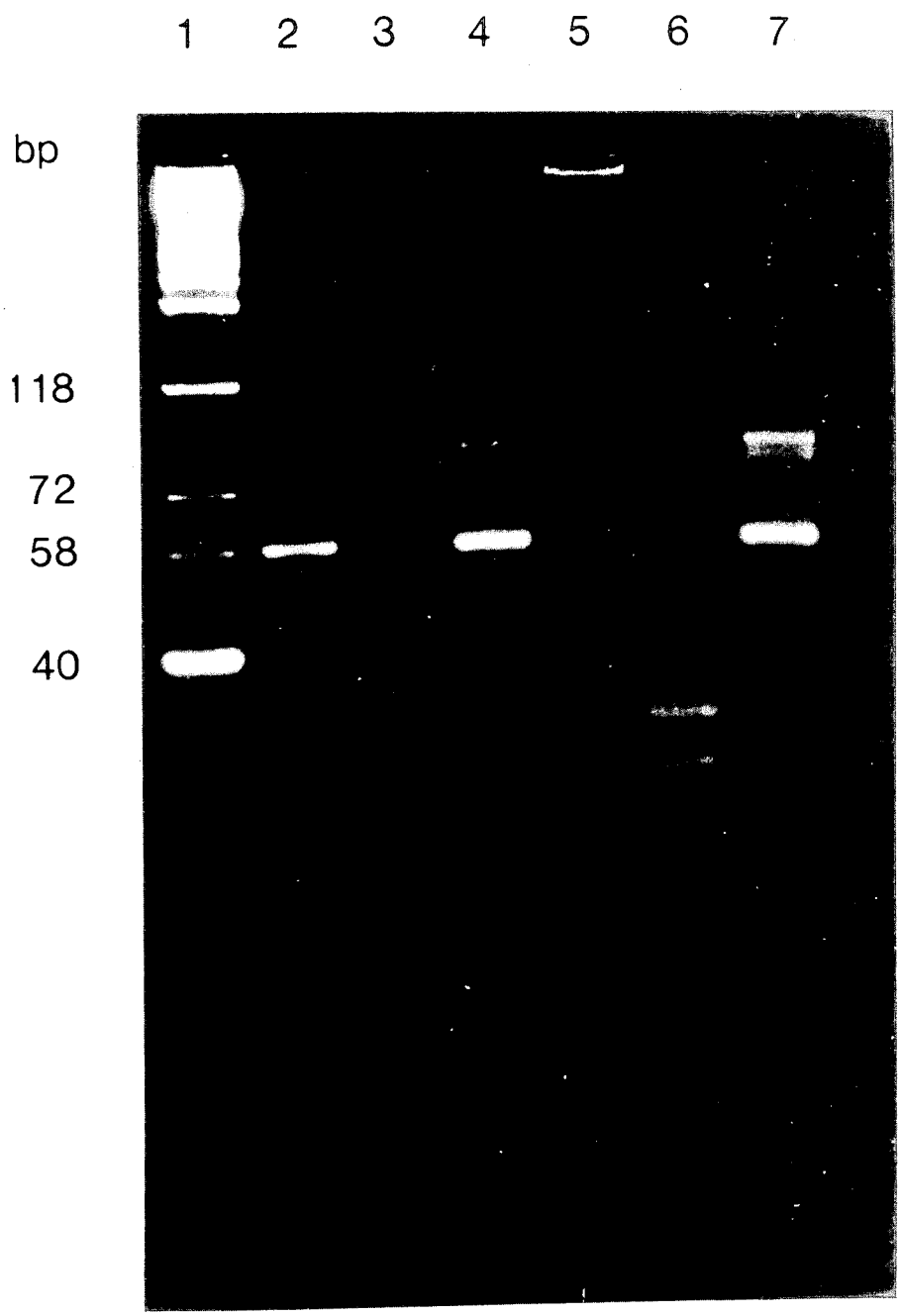
FIG. 10 illustrates a photograph of a 6% NuSieve agarose gel visualized using ethidium bromide and UV light. This photograph demonstrates amplification of a sub-fragment of a 110-bp amplification product which sub-fragment is an inner nested set within the 110-bp fragment.

FIG. 10 illustrates this gel illuminated with UV light and photographed through a red filter as is known in the art. Lane 1 is molecular weight markers. Lane 2 is an aliquot of the reaction described above. Lane 3 is an aliquot of a reaction identical to that described above, except that the original wild-type DNA was cleaved with DdeI prior to amplification. Lane 4 is an aliquot of a reaction identical to that described above, except that human DNA homozygous for the sickle betaglobin allele was treated with DdeI prior to amplification (the sickle allele does not contain a DdeI site in the fragment being amplified here). Lane 5 is an aliquot of a reaction identical to that described above, except that salmon sperm DNA was substituted for human DNA. Lane 6 is an aliquot of a reaction identical to that described above, except that the aliquot was treated with DdeI after amplification (DdeI should convert the 58-bp wild-type product into 27-and 31-bp fragments). Lane 7 is an aliquot of the Lane 4 material treated with DdeI after amplification (the 58-bp sickle product contains no DdeI site).

Detection of a 58-bp fragment representative of a singlecopy gene from one microgram of human DNA using only ethidium bromide staining of an agarose gel requires an amplification of about 500,000-fold. This was accomplished by using the two nested sets of oligonucleotide primers herein. The first set amplifies the 110-bp fragment and the inner nested set amplifies a sub-fragment of this product up to the level of convenient detection shown in FIG. 10. This procedure of using primers amplifying a smaller sequence contained within the sequence being amplified in the previous amplification process and contained in the extension products of the other primers allows one to distinguish the wild-type from the sickle allele at the betaglobin locus without resorting to either radiosotopic or otherwise cumbersome methodology such as that of Conner et al., Proc. Natl. Acad. Sci. U.S.A., 80:278 (1983) and Leary et al., Proc. Natl. Acad. Sci. U.S.A., 80:4045 (1983).

EXAMPLE 11

The present process is expected to be useful in detecting, in a patient DNA sample, a specific sequence associated with an infectious disease such as, e.g., Chlamydia using a biotinylated hybridization probe spanning the desired amplified sequence and using the process described in U.S. Pat. No. 4,358,535, supra. The biotinylated hybridization probe may be prepared by intercalation and irradiation of a partially double-stranded DNA with a 4'-methylene substituted 4,5'-8-trimethylpsoralen attached to biotin via a spacer arm of the formula:

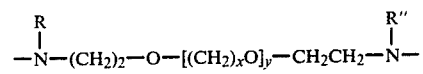

where R is —H or a —CHO group, R" is —H, x is a number from 1 to 4, and y is a number from 2 to 4, as described in U.S. Pat. No. 4,582,789 issued Apr. 15, 1986 to K. Mullis et al., the disclosure of which is incorporated herein by reference. Detection of the biotinyl groups on the probe may be accomplished using a streptavidin-acid phosphatase complex commercially obtainable from Enzo Biochemical using the detection procedures suggested by the manufacturer in its brochure. The hybridized probe is seen as a spot of precipitated stain due to the binding of the detection complex, and the subsequent reaction catalyzed by acid phosphatase, which produces a precipitable dye.

Deposit of Materials

The cell line SC-1 (CTCC #0082) was deposited on Mar. 19, 1985 with the American Type Culture Collection (ATCC), 12301 Parklawn Drive, Rockville, Md. 20852 USA, with ATCC Accession No. CRL#8756, The deposit of SC-1 was made pursuant to a contract between the ATCC and the assignee of this patent application, Cetus Corporation. The contract with ATCC provides for permanent availability of the progeny of this cell line to the public on the issuance of the U.S. patent describing and identifying the deposit or the publications or upon the laying open to the public of any U.S. or foreign patent application, whichever comes first, and for availability of the progeny of this cell line to one determined by the U.S. Commissioner of Patents and Trademarks to be entitled thereto according to 35 CFR §122 and the Commissioner's rules pursuant thereto (including 37 CFR §1.14 with particular reference to 886 OG 638). The assignee of the present application has agreed that if the cell line on deposit should die or be lost or destroyed when cultivated under suitable conditions, it will be promptly replaced on notification with a viable culture of the same cell line.

In summary, the present invention is seen to provide a process for amplifying one or more specific nucleic acid sequences using a chain reaction in which primer extension products are produced which can subsequently act as templates for further primer extension reactions. The process is especially useful in detecting nucleic acid sequences which are initially present in only very small amounts.

Other modifications of the above described embodiments of the invention which are obvious to those of skill in the area of molecular biology and related disciplines are intended to be within the scope of the following claims.

What is claimed is:

1. A process for amplifying at least one specific nucleic acid sequence contained in a nucleic acid or a mixture of nucleic acids wherein each nucleic acid consists of two separate complementary strands, of equal or unequal length, which process comprises:
    (a) treating the strands with two oligonucleotide primers, for each different specific sequence being amplified, under conditions such that for each different sequence being amplified an extension product of each primer is synthesized which is complementary to each nucleic acid strand, wherein said primers are selected so as to be sufficiently complementary to different strands of each specific sequence to hybridize therewith such that the extension product synthesized from one primer, when it is separated from its complement, can serve as a template for synthesis of the extension product of the other primer;
    (b) separating the primer extension products from the templates on which they were synthesized to produce single-stranded molecules; and
    (c) treating the single-stranded molecules generated from step (b) with the primers of step (a) under conditions that a primer extension product is synthesized using each of the single strands produced in step (b) as a template.

2. The process of claim 1, wherein steps (b) and (c) are repeated at least once.

3. The process of claim 1, wherein said step (b) is accomplished by denaturing.

4. The process of claim 3, wherein said denaturing is caused by heating.

5. The process of claim 1, wherein said step (b) is accomplished using the enzyme helicase.

6. The process of claim 1, wherein steps (a) and (c) are accomplished using an enzyme.

7. The process of claim 6, wherein said enzyme is selected from the group consisting of E. coli DNA polymerase I, Klenow fragment of E. coli DNA polymerase I, T4 DNA polymerase, reverse transcriptase wherein the template is RNA on DNA and the extension product is DNA, and an enzyme that after being exposed to a temperature of about 65°–90° C. forms said extension products at the temperature of reaction during steps (a) and (c).

8. The process of claim 7, wherein said nucleic acid is double stranded and its strands are separated by denaturing before or during step (a).

9. The process of claim 1, wherein said nucleic acid is DNA and said primers are oligodeoxyribonucleotides.

10. The process of claim 1, wherein said nucleic acid is messenger RNA.

11. The process of claim 1 wherein said mixture of nucleic acids used in step (a) is the product of step (c).

12. The process of claim 11, wherein the primers employed are different from the primers employed in the process for producing the product of step (c) used in step (a).

13. The process of claim 12, wherein the primers employed result in the amplification of a smaller sequence contained within the sequence being amplified in the process for producing the product of step (c) used in step (a).

14. The process of claim 1, wherein said steps are carried out simultaneously above room temperature using an enzyme that after exposed to a temperature of about 65°–90° C. forms said extension products at the temperature of reaction during steps (a) and (c).

15. The process of claim 1, wherein the two primers in steps (a) and (c) are each present in a molar ratio of at least 1000:1 primer:complementary strand.

16. The process of claim 1, wherein the nucleic acid sequence(s) to be modified is contained in a mixture of nucleic acids resulting from a chemical synthesis.

17. The process of claim 1, wherein at least one primer contains at least one nucleotide which is not complementary to the specific sequence to be amplified.

18. The process of claim 17 wherein one primer comprises an oligonucleotide with 20 complementary nucleotides and, at its 5′ end, a T7 promoter containing 26 noncomplementary nucleotides.

19. A process for amplifying a specific nucleic acid sequence contained in double-stranded DNA which process comprises:
    (a) separating the strands of the DNA by physical, chemical or enzymatic means;
    (b) treating the single strands with two oligodeoxyribonucleotide primers, in a molar excess of primer: its complementary strand, under conditions such that an extension product of each primer is synthesized, using E. coli DNA polymerase I or Klenow fragment thereof, which extension product is complementary to each DNA strand, wherein said primers are selected so as to be sufficiently complementary to different strands of each specific sequence to hybridize therewith such that the extension product synthesized from one primer, when it is separated from its complement, can serve as a template for synthesis of the extension product of the other primer;
    (c) separating the primer extension products from the templates on which they are synthesized to produce single-stranded molecules by physical, chemical or enzymatic means; and
    (d) treating the single-stranded molecules generated from step (c) with the two primers of step (b), in a molar excess of primer: its complementary molecule, under conditions such that a primer extension product is synthesized, using *E. coli* DNA polymerase I or Klenow fragment thereof, and using each of the single strands produced in step (c) as a template.

20. The process of claim 19, wherein steps (c) and (d) are repeated at least once.

21. The process of claim 1, wherein, due to the degeneracy of the genetic code, a collection of primers is employed for each complementary strand, the sequence of one of which primers is exactly complementary to said complementary strand over the length of the primer.

* * * * *

UNITED STATES PATENT AND TRADEMARK OFFICE
CERTIFICATE OF CORRECTION

PATENT NO.   : 4,683,202
DATED        : July 28, 1987
INVENTOR(S)  : Kary B. Mullis It is certified that error appears in the above-identified patent and that said Letters Patent is hereby corrected as shown below:

<u>Title page,</u>
After [*] Notice, please replace "The portion of the term of this patent subsequent to Jul. 28, 2004 has been disclaimed." with -- This patent is subject to a terminal disclaimer. --

Signed and Sealed this

First Day of July, 2003

JAMES E. ROGAN
*Director of the United States Patent and Trademark Office*

UNITED STATES PATENT AND TRADEMARK OFFICE
CERTIFICATE OF CORRECTION

| | | |
|---|---|---|
| PATENT NO. | : 4,683,202 | Page 1 of 1 |
| APPLICATION NO. | : 06/791308 | |
| DATED | : July 28, 1987 | |
| INVENTOR(S) | : Kary B. Mullis | |

It is certified that error appears in the above-identified patent and that said Letters Patent is hereby corrected as shown below:

TITLE PAGE, after "[*] Notice:" replace "The portion of the term of this patent subsequent to Jul. 28, 2004 has been disclaimed." with --This patent is subject to a terminal disclaimer.--

Signed and Sealed this

Fifth Day of June, 2007

JON W. DUDAS
*Director of the United States Patent and Trademark Office*

REEXAMINATION CERTIFICATE (1388th)

United States Patent [19]

Mullis

[11] B1 4,683,202

[45] Certificate Issued * Nov. 27, 1990

[54] PROCESS FOR AMPLIFYING NUCLEIC ACID SEQUENCES

[75] Inventor: Kary B. Mullis, Kensington, Calif.

[73] Assignee: Cetus Corporation

Reexamination Request:
No. 90/001,903, Dec. 6, 1989
No. 90/001,955, Mar. 9, 1990

Reexamination Certificate for:
Patent No.: 4,683,202
Issued: Jul. 28, 1987
Appl. No.: 791,308
Filed: Oct. 25, 1985

[*] Notice: The portion of the term of this patent subsequent to Jul. 28, 2004 has been disclaimed.

[51] Int. Cl.$^5$ ............... C12P 19/34; C12N 15/00; C12N 1/00; C07H 21/04
[52] U.S. Cl. ............................ 435/91; 435/91; 435/172.3; 435/317.1; 536/27; 536/28; 536/29; 935/17; 935/18; 935/16
[58] Field of Search ............... 435/91, 172.3, 317.1; 536/27, 28, 29; 935/17, 18

[56] References Cited

U.S. PATENT DOCUMENTS

| | | | |
|---|---|---|---|
| 4,555,486 | 11/1985 | Bahl et al. | 435/91 |
| 4,582,788 | 4/1986 | Erlich | 435/6 |
| 4,737,462 | 4/1988 | Mark et al. | 435/252.33 |
| 4,853,332 | 8/1989 | Mark et al. | 435/252.33 |

OTHER PUBLICATIONS

Khorana, Progress Report, Grant No. CA11981-02, 09-01-1971 through 08-31-1972.
Zoller et al; DNA 3: 479 (1984).
BioLogicals Advertisement; Science, Dec. 11, 1981.
New England Biolabs Catalog, 1983/84, p. 29.
*Molecular Cloning A Laboratory Manual,* 1982, Maniatis et al, Cold Spring Harbor Laboratory, Cold Spring Harbor, NY, pp. 113–132 and 230–238.
Kaledin et al; Biokhimiya 45(4), 644 (1980), published by Plenum Publishing Corporation.
Chien et al; J. Bacteriol. 127: 1550 (1976).
Anonymous; Nature 341: 570 (1989).
Kleppe et al; J. Mol. Biol. 56: 341 (1976).
Khorana et al; J. Mol. Biol. 72: 209 (1972).
Panet et al; J. Biol. Chem. 249: 5213 (1974).
Besmer et al., 1972, *J. Mol. Biol.* 72:503–522.

*Primary Examiner*—James Martinell

[57] ABSTRACT

The present invention is directed to a process for amplifying any desired specific nucleic acid sequence contained in a nucleic acid or mixture thereof. The process comprises treating separate complementary strands of the nucleic acid with a molar excess of two oligonucleotide primers, and extending the primers to form complementary primer extension products which acts as templates for synthesizing the desired nucleic acid sequence. The steps of the reaction may be carried out stepwise or simultaneously and can be repeated as often as desired.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-21 is confirmed.

* * * * *